United States Patent [19]

Urbano et al.

[11] Patent Number: 5,976,088
[45] Date of Patent: Nov. 2, 1999

[54] ULTRASOUND IMAGING SYSTEMS AND METHODS OF INCREASING THE EFFECTIVE ACQUISITION FRAME RATE

[75] Inventors: Joseph A. Urbano, Mt. Holly, N.J.; Christopher B. Knell, North Wales; Kevin S. Randall, Ambler, both of Pa.; Andrew J. Wood, Mt. Holly, N.J.

[73] Assignee: Ecton, Inc., Ambler, Pa.

[21] Appl. No.: 09/262,568

[22] Filed: Mar. 4, 1999

Related U.S. Application Data

[62] Division of application No. 09/103,878, Jun. 24, 1998.

[51] Int. Cl.$^6$ ...................................................... A61B 8/00
[52] U.S. Cl. ........................................... 600/443; 600/450
[58] Field of Search ..................................... 600/437, 440, 600/442, 443, 447, 450, 454, 458

[56] References Cited

U.S. PATENT DOCUMENTS

| | | |
|---|---|---|
| 3,603,729 | 9/1971 | Sperber . |
| 4,335,427 | 6/1982 | Hunt et al. . |
| 4,337,481 | 6/1982 | Mick et al. . |
| 4,444,196 | 4/1984 | Stein . |
| 4,585,008 | 4/1986 | Jarkewicz . |
| 4,729,379 | 3/1988 | Ohe . |
| 4,750,367 | 6/1988 | Bernatets . |
| 4,751,846 | 6/1988 | Dousse . |
| 4,785,818 | 11/1988 | Hardin . |
| 4,846,188 | 7/1989 | Yoshioka . |
| 4,878,115 | 10/1989 | Elion . |
| 4,887,306 | 12/1989 | Hwang et al. . |
| 4,888,694 | 12/1989 | Chesarek . |
| 5,000,182 | 3/1991 | Hinks . |
| 5,060,515 | 10/1991 | Kanda et al. . |
| 5,099,847 | 3/1992 | Powers et al. . |
| 5,103,823 | 4/1992 | Acharya et al. . |
| 5,142,558 | 8/1992 | Franciose . |
| 5,152,290 | 10/1992 | Freeland . |
| 5,215,094 | 6/1993 | Franklin et al. ......................... 600/454 |
| 5,251,027 | 10/1993 | LaBeau . |
| 5,255,683 | 10/1993 | Monaghan . |
| 5,325,858 | 7/1994 | Moriizumi . |
| 5,357,580 | 10/1994 | Forestieri et al. . |
| 5,425,366 | 6/1995 | Reinhardt et al. . |
| 5,456,257 | 10/1995 | Johnson et al. . |
| 5,467,770 | 11/1995 | Smith et al. ............................ 600/454 |
| 5,476,096 | 12/1995 | Olstad et al. . |
| 5,482,046 | 1/1996 | Deitrich .................................. 600/458 |
| 5,564,428 | 10/1996 | Soernmo et al. . |
| 5,595,179 | 1/1997 | Wright et al. . |
| 5,619,995 | 4/1997 | Lobodzinski ............................ 600/425 |
| 5,647,360 | 7/1997 | Bani-Hashemi et al. . |
| 5,666,955 | 9/1997 | Kondo et al. ............................ 600/440 |
| 5,797,846 | 8/1998 | Seyed-Bolorforosh et al. ........ 600/447 |

*Primary Examiner*—Francis J. Jaworski
*Assistant Examiner*—Ali M. Imam
*Attorney, Agent, or Firm*—Akin, Gump, Strauss, Hauer & Feld, L.L.P.

[57] ABSTRACT

Ultrasound imaging data obtained from anatomic structures which have periodic physiologic motion that define successive physiologic cycles is packaged into image loops. Each image loop includes frame data representing a plurality of image frames acquired at spaced time intervals within a physiologic cycle. The image loops may be transmitted to a remote location for playback in real-time or pseudo real-time. Also provided is a scheme for increasing the effective acquisition frame rate in a medical ultrasound imaging system which acquires imaging data of an anatomic structure having periodic physiologic motion that defines successive physiologic cycles.

9 Claims, 22 Drawing Sheets

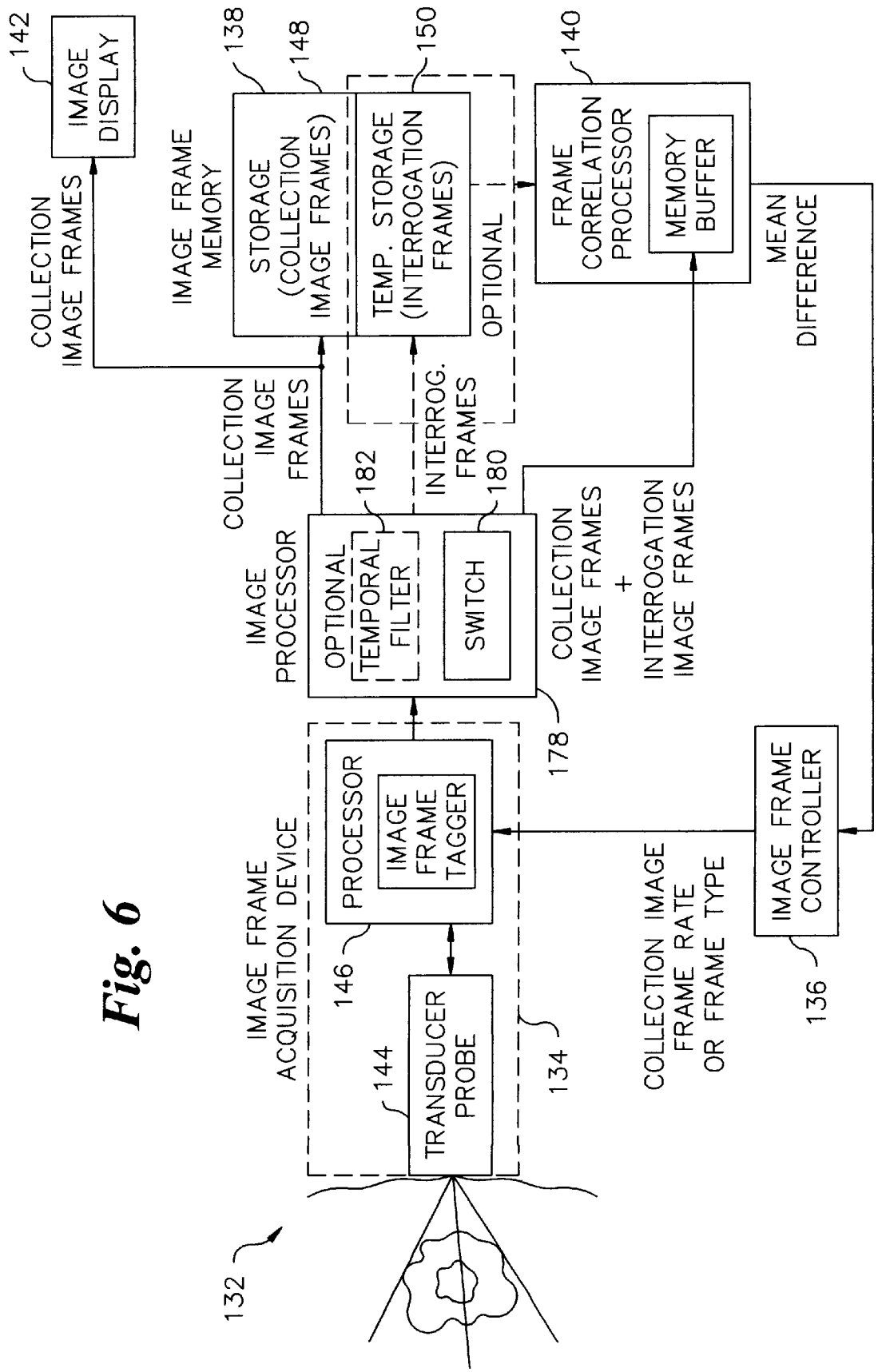

F = FULL-RESOLUTION FRAME (COLLECTION IMAGE FRAME)
I = INTERROGATION FRAME

F1
| 8 | 7 |
|---|---|
| 5 | 4 |

F2
| 8 | 6 |
|---|---|
| 5 | 4 |

MEAN DIFFERENCE = 0.25

F5
| 8 | 7 |
|---|---|
| 5 | 4 |

I37
| 8 | 2 |
|---|---|
| 1 | 3 |

MEAN DIFFERENCE = 2.5

| MEAN DIFFERENCE | FRAME RATE (2 RATES) | FRAME RATE (4 RATES) |
|---|---|---|
| 0 - .5 | SLOW | VERY SLOW |
| .6 - 1.5 | SLOW | SLOW |
| 1.6 - 3 | FAST | FAST |
| 3.1 - 36 | FAST | VERY FAST |

| COLLECTION IMAGE FRAME | TIME BETWEEN ADJACENT COLLECTION IMAGE FRAMES (IN NUMBER OF TIME PERIODS) |
|---|---|
| F1 | 1 |
| F2 | 1 |
| F3 | 4 |
| F4 | 4 |
| F5 | 4 |
| F6 | 1 |
| F7 | 1 |
| F8 | 1 |
| ⋮ | ⋮ |
| FN | |

*Fig. 12*

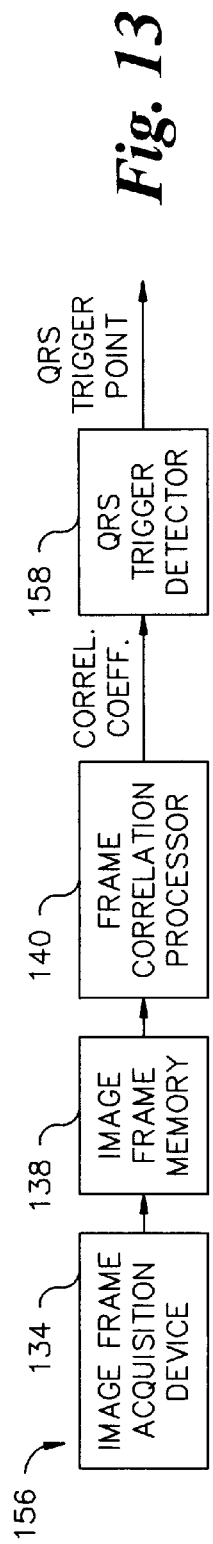
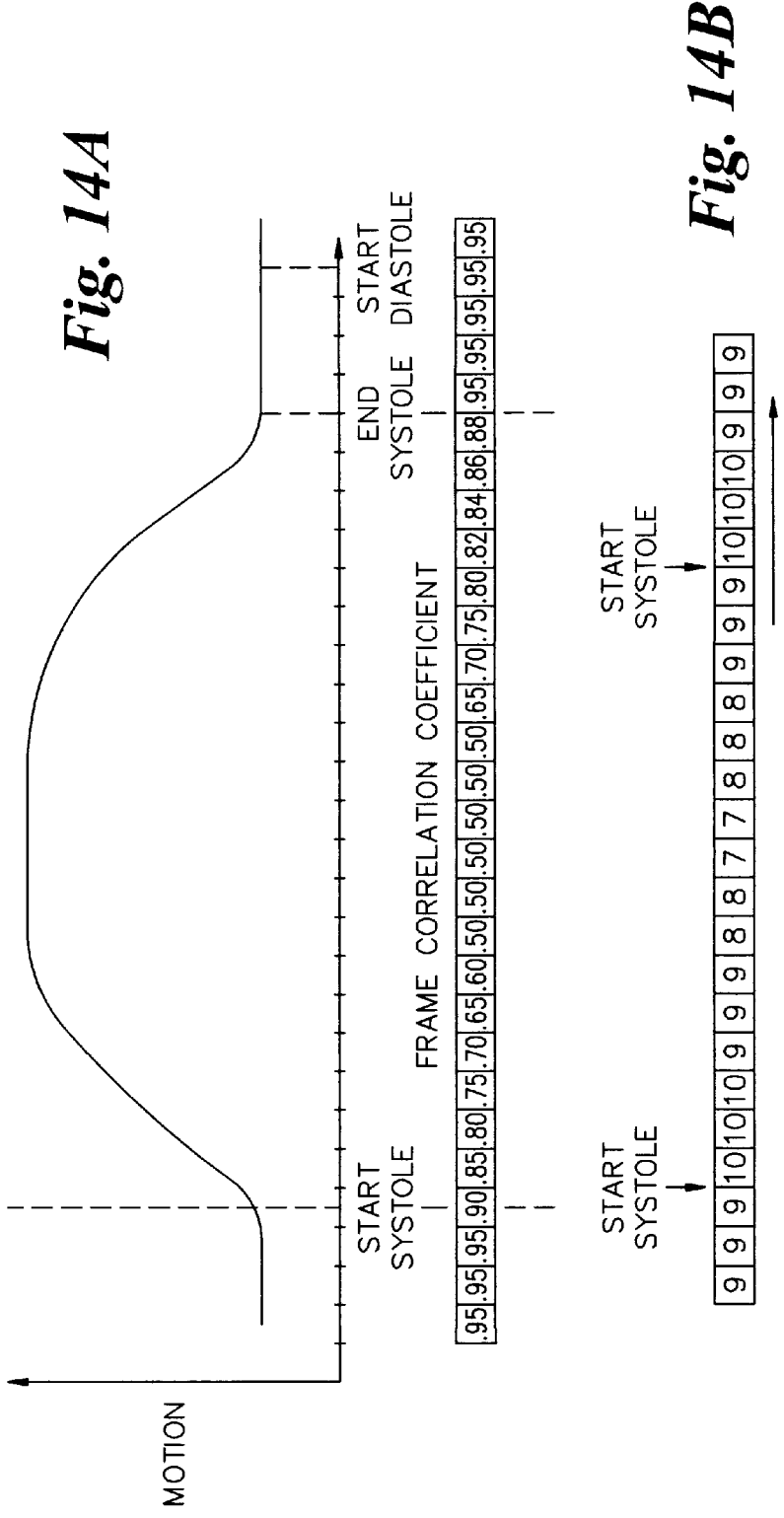

Fig. 30A REAL-TIME TRANSMISSION

| PHYSIOLOGIC CYCLE → BUFFER CONTENTS FIG. 28 / FIG. 29 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| A/B  A | 1 | 2 | 3 | 4 | 5 | 6 | 7 | 8 | 9 | 10 | 11 | 12 | 13 | 14 |
| B/A  B | — | 1 | 2 | 3 | 4 | 5 | 6 | 7 | 8 | 9 | 10 | 11 | 12 | 13 |
| C/D  C | — | — | 1 | 2 | 3 | 4 | 5 | 6 | 7 | 8 | 9 | 10 | 11 | 12 |
| D/C  D | — | — | — | 1 | 2 | 3 | 4 | 5 | 6 | 7 | 8 | 9 | 10 | 11 |

Fig. 30B PSEUDO-REAL TIME TRANSMISSION

| PHYSIOLOGIC CYCLE → BUFFER CONTENTS FIG. 28 / FIG. 29 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| A/B  A | 1 | 2 | 3 | 4 | 5 | 6 | 7 | 8 | 9 | 10 | 11 | 12 | 13 | 14 |
| B/A  B |  | 1 | 1 | 1 | 4 | 4 | 4 | 7 | 7 | 7 | 10 | 10 | 10 | 13 |
| C/D  C |  |  | RECEIVING 1 | RECEIVING 1 | RECEIVING 1 | RECEIVING 4 | RECEIVING 4 | RECEIVING 4 | RECEIVING 7 | RECEIVING 7 | RECEIVING 7 | RECEIVING 10 | RECEIVING 10 | RECEIVING 10 |
| D/C  D |  |  |  |  | 1 | 1 | 1 | 4 | 4 | 4 | 7 | 7 | 7 | 10 |

ULTRASOUND IMAGING SYSTEMS AND METHODS OF INCREASING THE EFFECTIVE ACQUISITION FRAME RATE

CROSS REFERENCE TO RELATED APPLICATION

This application is a division of copending application Ser. No. 09/103,878, filed Jun. 24, 1998, originally entitled "ULTRASONIC IMAGING SYSTEMS AND METHODS, the entire disclosure of which is incorporated herein by reference.

BACKGROUND OF THE INVENTION

Ultrasound imaging involves the display of information obtained from reflections of (echoes of) pulses of ultrasonic waves directed into the body. These echoes contain information about the underlying structure of the tissue and blood flow in the region exposed to ultrasound waves. The sophistication and capabilities of ultrasound imaging systems have increased dramatically in recent years, resulting in bulkier and costlier systems which collect an ever increasing volume of data for each imaging session. The explosion in system cost and amount of data collected creates significant problems for the health care industry which must control equipment costs, data storage costs, and labor costs associated with diagnostic testing. Today, many rural and remotely located health care facilities cannot afford to purchase, install or maintain the bulky and costly sophisticated ultrasound imaging systems presently on the market. Furthermore, physicians do not wish to use stripped down or otherwise inferior versions of current systems, since the sophisticated capabilities are often necessary to obtain the most accurate diagnosis possible. Accordingly, there is a significant and unmet need for an ultrasound imaging system which is physically small and/or portable, which collects data in a manner that minimizes storage needs, and which is significantly less expensive than current state of the art systems, yet which provides diagnostic capabilities that are equal to or better than existing bulky and costly full feature systems. The present invention fulfills such needs.

BRIEF SUMMARY OF THE INVENTION

The present invention provides systems and methods for obtaining ultrasound imaging data at an adjustable collection image frame rate, as well as at an adjustable acquisition rate.

The present invention also provides systems and methods to use a frame correlation process acting on ultrasound imaging data to locate the occurrence of a predetermined event in a physiologic cycle.

The present invention further provides systems and methods to reduce speckle in full motion ultrasound image data by filtering image frames of each physiologic cycle across the cycles, instead of filtering from frame to frame.

The present invention also provides a scheme for packaging ultrasound imaging data obtained from anatomic structures which have periodic physiologic motion that define successive physiologic cycles. The imaging data is packaged into image loops. Each image loop includes frame data representing a plurality of image frames acquired at spaced time intervals within a physiologic cycle. A communication scheme is provided for transmitting the image loops to a remote location for playback in real-time or pseudo real-time.

The present invention also provides a scheme for increasing the effective acquisition frame rate in a medical ultrasound imaging system which acquires imaging data of an anatomic structure having periodic physiologic motion that defines successive physiologic cycles.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 6 is a schematic block diagram of a medical ultrasound imaging system in accordance with the present invention which has an adjustable collection image frame rate;

FIG. 12 shows a scheme for collecting data representing time between adjacent collection image frames for use with the system of FIG. 6;

FIG. 13 is a schematic block diagram of a system for locating the occurrence of a predetermined event in a physiologic cycle in accordance with the present invention;

FIGS. 14A is a graph of a portion of a heart cycle shortly before, during, and shortly after systole which indicates relative motion of the heart being imaged, and also shows a table of corresponding frame correlation coefficients obtained in this region of the heart cycle;

FIG. 14B is a table showing corresponding mean first difference values obtained from experimental heart image data for one complete heart cycle;

FIGS. 30A and 30B show sample contents of memory buffers in the systems of FIGS. 28 and 29 for a plurality of successive physiologic cycles.

DETAILED DESCRIPTION OF THE INVENTION

Figure 1:
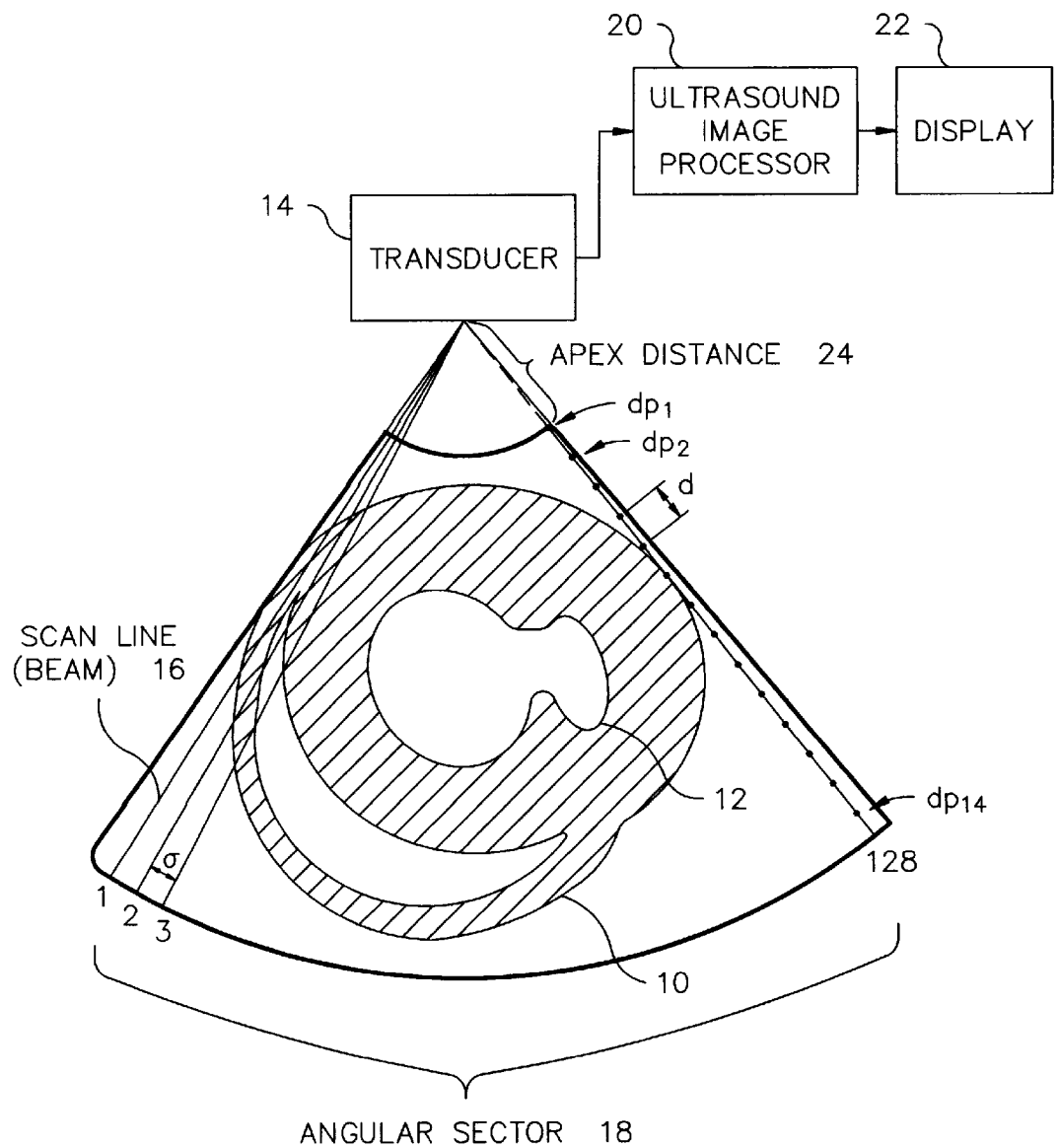
FIG. 1 is a sample ultrasound sector scan image of an anatomic structure and shows parameters of an ultrasound scan.

In the drawings, like numerals are used to indicate like elements throughout. As summarized above, the invention includes a plurality of different features which may be used individually, or in combination within a single piece of ultrasound equipment. Each feature is described below in its appropriate section.

As background to the present invention, prior art FIG. 1 shows a sample ultrasound sector scan image of an anatomic structure 10, as well as the parameters of the scan. The structure 10 is a heart, and feature 12 is an outline of a heart chamber. The image is obtained using a conventional transducer 14 which forms a plurality of scan lines or beams 16 that traverse an angular sector 18 in a plane. There are 128 scan lines 16 per image in the example of FIG. 1. The scan line data are processed by ultrasound image processor 20 and viewed on display 22 as a succession of image frames, in a conventional manner. The image formed by each successive pass through the angular sector 18 (e.g., 128 scan lines in the example of FIG. 1) defines one image frame. The "image frame rate" of an ultrasound device is the number of image frames obtained per unit time. A typical frame rate may range from 15 to 45 frames per second (FPS). The "image frame period" is the amount of time between adjacent frames.

The parameters of the scanning process may be further defined as follows:

Apex Distance 24—This is the distance from the transducer's transmitter emission point to the region of the image where data collection begins.

Scan Line data points (dp)—These are data points along each scan line 16. Each data point ultimately represents a pixel value on the display 22. For illustration purposes, fourteen data points $dp_1$–$dp_{14}$ are shown along the 128th scan line. A typical scan line 16 actually may have 300–400 data points.

Distance between data points (d)—This is the distance between adjacent data points in each scan line 16.

θ—This is the angle between adjacent scan lines 16. For example, if the angular sector 18 traverses a 70 degree arc, and there are 128 scan lines for the sector, then θ equals about 0.55 degrees. θ is related to scan line density (i.e., number of scan lines in a frame), also referred to herein as the image frame "resolution." θ decreases as scan line density increases.

The present invention is particularly useful for imaging anatomic structures which exhibit periodic physiological motion wherein the motion defines successive periodic cycles. The heart and lungs are examples of anatomic structures which have periodic cycles. Since the heart cycle (cardiac cycle) is used to illustrate certain features of the present invention, some background on the heart cycle is provided to further understand the invention.

Figure 2:
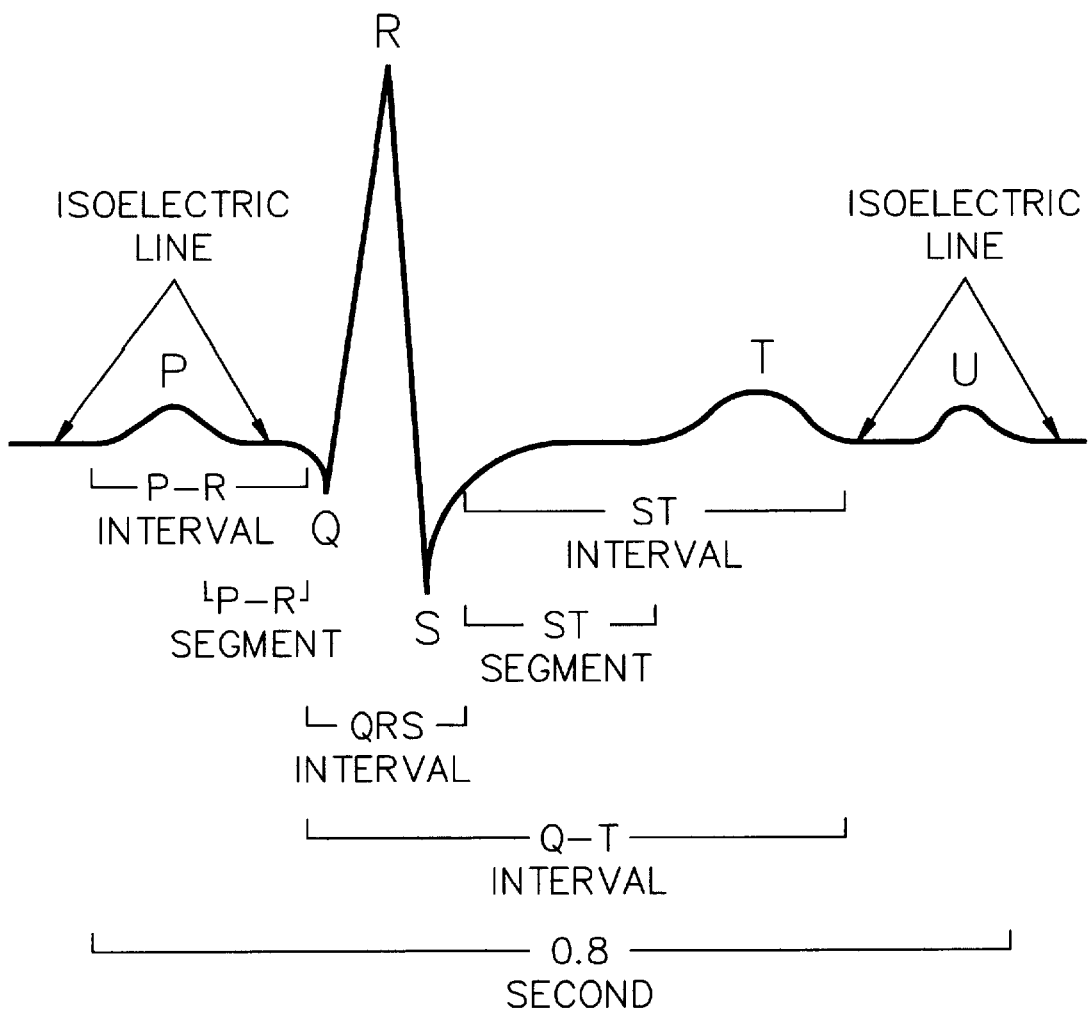
FIG. 2 is an electrocardiogram of the human heart.

FIG. 2 shows a normal electrocardiogram (ECG or EKG) of the human heart. The EKG is a scalar representation that shows deflections resulting from atrial and ventricular activity as changes in the magnitude of voltage and polarity with time. The deflections are referred to as "waves." For example, the first deflection is the P wave. One particular point of interest of the EKG is the QRS interval or QRS complex, and particularly the peak of the R wave, also referred to as the QRS trigger. The heart cycle is defined as the period from the beginning of one heart beat to the beginning of the next heart beat. The heart cycle has two important time intervals during each cycle, namely the systole and diastole. During diastole, the left ventricle fills with blood. During systole, the left ventricle contracts to pump the blood out of the heart. The so-called "systolic time interval" is the interval from the onset of the QRS interval to the aortic component of the second heart sound. Most of the remaining time of the heart cycle comprises the diastole. During systole, there is a large amount of motion in the anatomic parts of the heart, whereas there is relatively less motion during diastole. Diagnostic heart studies are often concerned with the action of anatomic structures during systole. The QRS trigger provides a convenient way to detect the onset of systole and is often used to control ultrasound equipment for capturing image data.

Storage and Packaging/Formatting of Ultrasound Imaging Data

All ultrasound imaging systems have memory for collecting and storing image data. The image data may be stored as raw data representing the pixels obtained from data points along each scan line 16 shown in FIG. 1, or the image data may be stored as processed frame data, in the same manner as a frame of video. Each ultrasound system has its own data storage structure and memory structure. Accordingly, it is sometimes difficult or impossible to view image data on one ultrasound system which is acquired on a different system. Likewise, stored image data often cannot be easily shared among systems, unless the data storage structure is well understood and any necessary data conversion steps are performed. The present invention addresses these deficiencies in the prior art by providing a packaging/formatting structure for ultrasound imaging data, and particularly, for ultrasound imaging data obtained from an anatomic structure having periodic physiological motion.

Figure 3A:
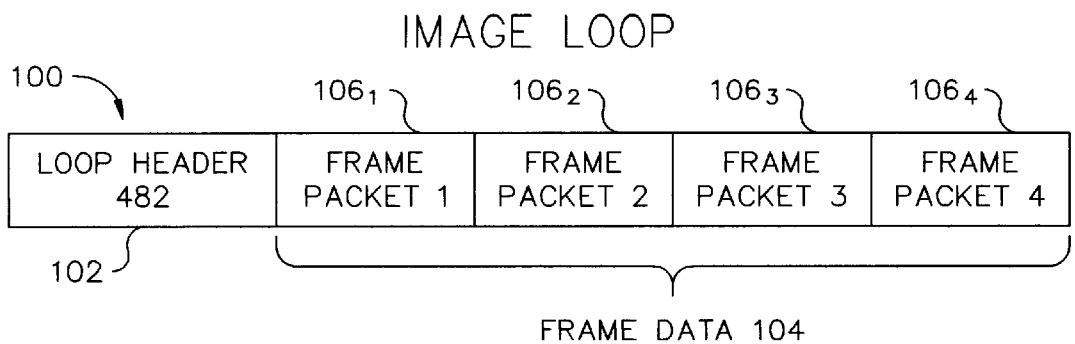
FIGS. 3A–3C show the structure of image loops in accordance with the present invention.

The imaging data, in accordance with the present invention, is stored and packaged or formatted as image loops. Each image loop includes frame data representing a plurality of image frames acquired at spaced time intervals within a physiologic cycle. FIG. 3A shows an image loop 100. The image loop 100 includes a loop header 102 and the frame data 104 for one physiologic cycle. In the simplified example of FIG. 3A provided for illustration purposes, the frame data comprises four image frames acquired during each cycle. The image frame data 104 is packaged as a plurality of frame packets $106_1$–$106_4$, described in more detail below with respect to FIG. 3B. The loop header 102 may be used to identify the loop by number, for example, cycle number 482 in a stream of collected data.

Consider an example wherein the anatomic structure is the heart, the physiologic cycle is the heart cycle, and the image loop 100 includes a plurality of image frames acquired for one physiologic cycle at a predefined time relative to a QRS trigger. For example, the image frames may be acquired from one QRS trigger to the next, or from a few milliseconds after the QRS trigger to a few milliseconds after the next QRS trigger. If the frame rate of the acquisition equipment is 30 FPS and the heart cycle is about one second, then there will be about 30 frame packets in each image loop 100 (as opposed to the four shown in FIG. 3A).

Figure 3B:
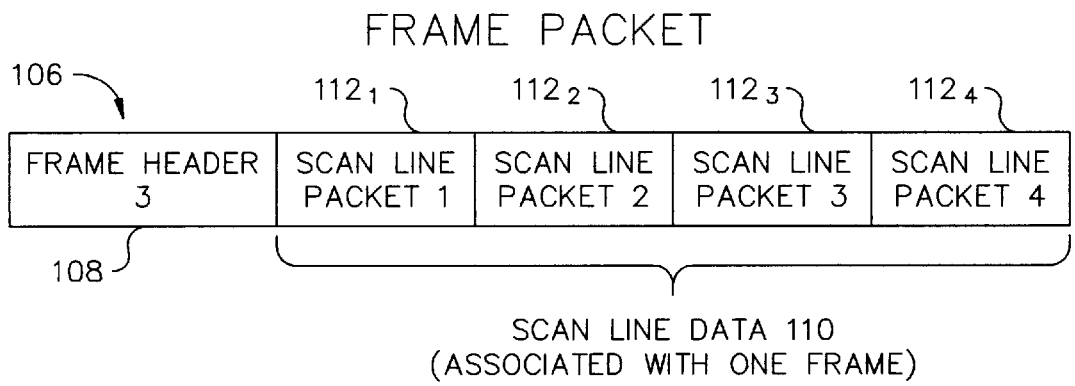

FIG. 3B shows a frame packet 106. Each frame packet 106 includes a frame header 108 and the scan line data associated with the frame. The scan line data 110 is packaged as a plurality of scan line packets $112_1$–$112_4$, described in more detail below with respect to FIG. 3C. The frame header 108 identifies the frame by number, for example, frame number 3 in the sequence of four frame packets of FIG. 3A, or frame number 3 in a sequence of 30 frame packets in the heart example described above. Alternatively, the frame numbers may begin with zero. In the heart cycle example, frame zero would be acquired at the QRS trigger or a predetermined time period displaced therefrom.

Figure 3C:
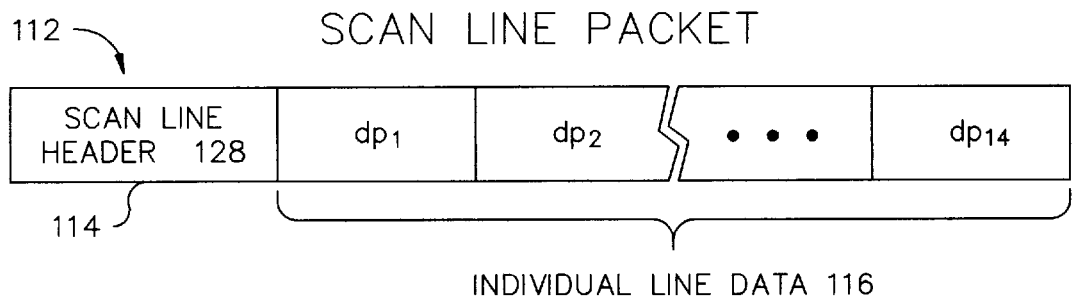

FIG. 3C shows a scan line packet 112. Each scan line packet 112 includes a scan line header 114 and the individual line data 116 associated with the scan line. The scan line header 114 comprising a line number representing a position within a scan sector, such as the last scan line shown in FIG. 1 (scan line 128). The individual line data represents the data points along the scan line, such as $dp_1$–$dp_{14}$ shown in FIG. 1.

The loop header 102, the frame header 108 and the scan line header 114 thus function much like the identification portion or ID tag of a data packet in a digital communication scheme. These headers may also be used to store additional information to assist in processing the image data. For example, the loop header 102 may also include any of the following types of information:

(1) Timing of the image loop with respect to a known point of the physiological cycle, such as the timing with respect to the QRS trigger.
(2) Time interval of the image loop. This may be used for playback control.
(3) Type of physiologic cycle (e.g., heart cycle, respiratory cycle)
(4) Geometric parameters of the ultrasound scan (e.g., apex distance 24, distance between data points (d), θ).
(5) Number of frames or frame packets in the loop.
(6) Type of scan line data (e.g., B-mode data, color flow, harmonic mode)

The frame header 108 may also include any of the following types of information:

(1) Time between adjacent, successively acquired or collected frames (i.e., current and previous frame). This information is particularly important when image frames are acquired or collected at different frame rates. During playback, this information is used to determine how long the frame should persist on the display screen before being replaced by the next frame.
(2) Geometric parameters of the ultrasound scan, especially if one or more parameters vary on a frame-to-frame basis. If the parameters are the same for all frames, then they should be placed in the loop header to avoid redundancy of information.
(3) Number of scan lines or scan line packets in the frame packet (i.e., scan line density).
(4) Whether the image frame is a collection image frame or an interrogation image frame (see discussion below).

The scan line header 114 may also include any of the following types of information:

(1) Type of scan line data
(2) Number of data points in the scan line or scan line packet.
(3) Number of bits per data point sample.

Additional types of information may be included in the loop, frame and scan line headers to assist in processing the image data.

One preferred embodiment of the invention for use in collecting image data of a heart cycle synchronizes frame acquisition using the QRS trigger point, wherein each image loop goes from one QRS trigger point (or a predetermined time with respect to the QRS trigger point) to the next QRS trigger point. Alternatively, if no triggering event is used, an image loop may be acquired every predetermined number of seconds. If no triggering event is used, sufficient frames should be collected with each image loop to ensure that each loop includes at least one full physiologic cycle of data.

Furthermore, an image loop as defined herein, starts at a first predefined time with respect to a predetermined event in a physiologic cycle and ends at a second predefined time with respect to the predetermined event in the physiologic cycle or in one or more successive physiologic cycles. In one preferred scheme, the image loop has a length of one physiologic cycle. Alternatively, the image loop may have a length greater or less than one physiologic cycle, such as one-half cycle, 1½ cycles, or two cycles. For example, an image loop may consist of only the systole portion of a heart cycle, or may consist of two full heart cycles. When the image loop has a length of one physiologic cycle, the image loop may start at the beginning of a first physiologic cycle and end at the end of the same physiologic cycle, right before the start of the next physiologic cycle. However, the image loop is not necessarily acquired from the same physiologic cycle. The image loop for the single physiologic cycle may, for example, be made up of image frames from the second half of a first physiologic cycle and the first half of the subsequent physiologic cycle. The frames in the image loop are still ordered from the start of the physiologic cycle to the end of the physiologic cycle, as determined by the collection time of the image frame with respect to the triggering event.

Consider a simplified example of four physiologic cycles, A, B, C and D, wherein four image frames 1–4 are taken per cycle. The time sequence of image cycles would be as follows:

A1 A2 A3 A4 B1 B2 B3 B4 C1 C2 C3 C4 D1 D2 D3 D4

The first three image loops may be packaged by the single cycles, as follows:

Image loop 1—A1 A2 A3 A4
Image loop 2—B1 B2 B3 B4
Image loop 3—C1 C2 C3 C4

Alternatively, if data capturing/storage does not begin until the middle of the first physiologic cycle, the first three image loops may be packaged as follows:

Image loop 1—B1 B2 A3 A4
Image loop 2—C1 C2 B3 B4
Image loop 3—D1 D2 C3 C4

Since image data is presumed to be relatively similar from cycle to cycle, there should theoretically be very little difference between the respective image loops in the single cycle packaging scheme vs. the adjacent cycle packaging scheme, assuming that no sudden events are occurring in the imaged anatomic structure.

Figure 4:
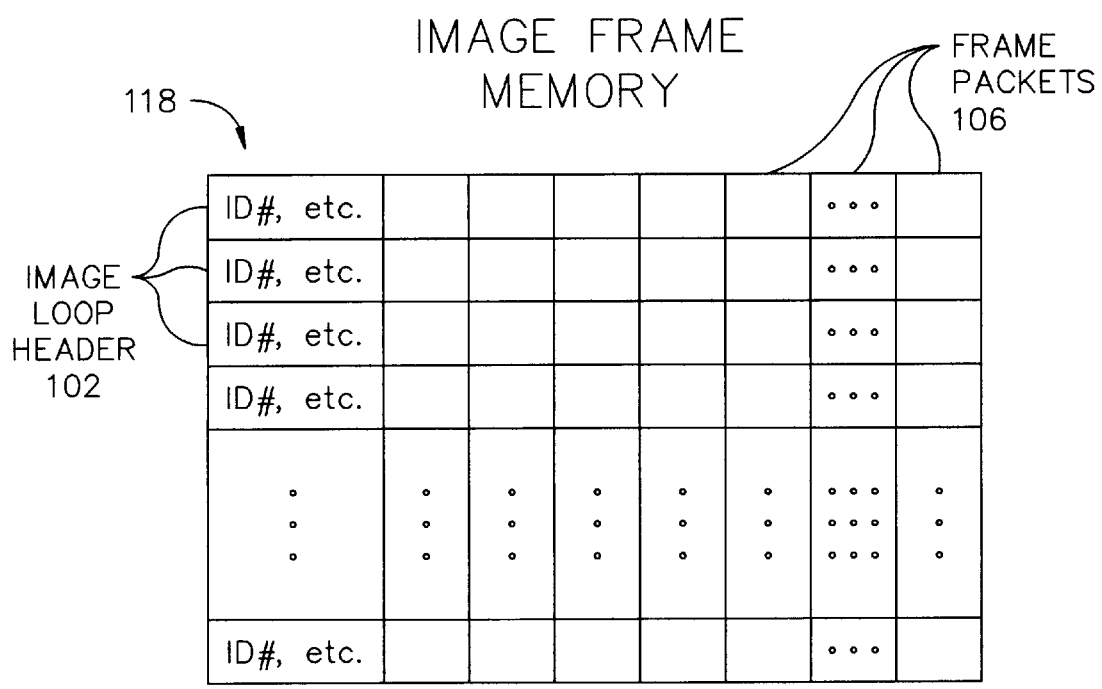
FIG. 4 is an image frame memory for storing ultrasound image frame data as a series of image loops shown in FIGS. 3A–3C.

FIG. 4 is an image frame memory 118 for storing ultrasound image frame data as a series of image loops 100. Each image loop 100 includes an image loop header 102 and a plurality of frame packet 106.

By packaging the image data in image loops, the image data becomes very easy to manipulate and to communicate to a remote site. Disparate equipment can easily interpret the image data for display. Image loops simplify memory management of the image data because selected portions of data can be easily identified for storage, retrieval or display.

Figure 5:
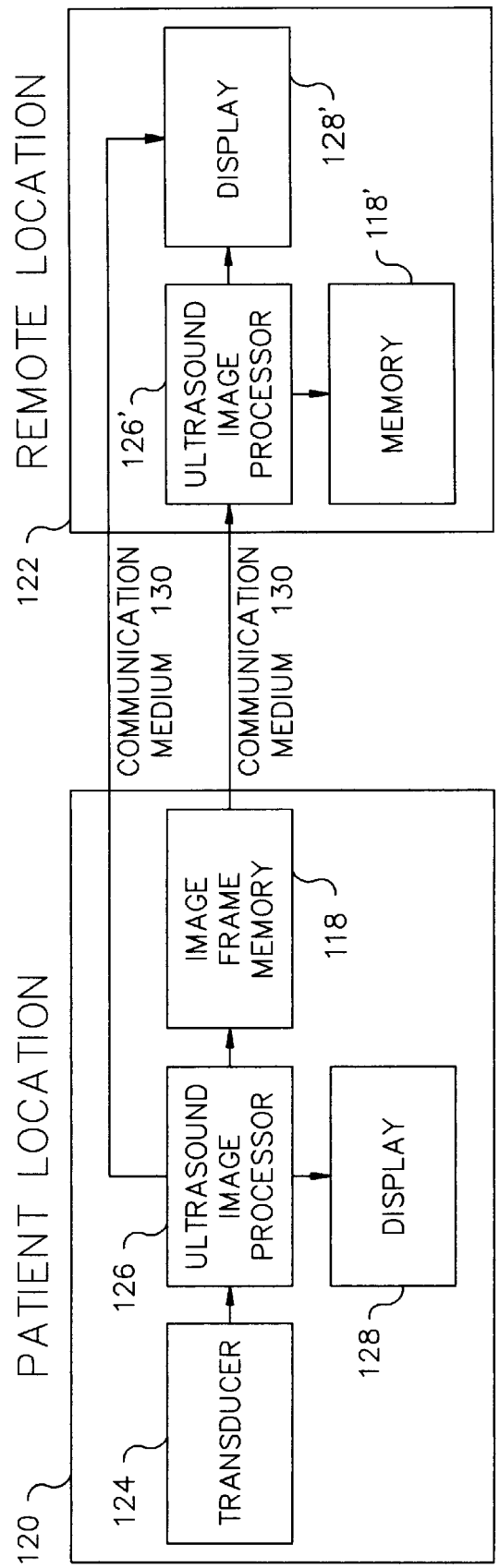
FIG. 5 is a schematic block diagram of a communication environment for transmitting the image loops from an image acquisition location to a remote location.

FIG. 5 shows a patient location 120 and a remote location 122. Ultrasound image data is acquired from a transducer 124, and the raw image data is fed into an ultrasound image processor 126 which formats the data into image loops 100, as described above. All of the information associated with an image loop 100 is conventional, and thus no additional explanation is provided on how to capture such information. However, heretofore, such information was not captured and used for packaging or formatting image data in the image loop format.

After creation, the image loops 100 may be stored locally in the image frame memory 118 and/or viewed on display 128. The image loops 100 may also be communicated to the remote location 122 via communication or transmission medium 130 either directly from the processor 126, or from the image frame memory 118. Upon receipt at the remote location 122, the image loops 100 are processed by ultrasound image processor 126' and stored locally in the image frame memory 118' and/or viewed on display 128'.

Figure 28:
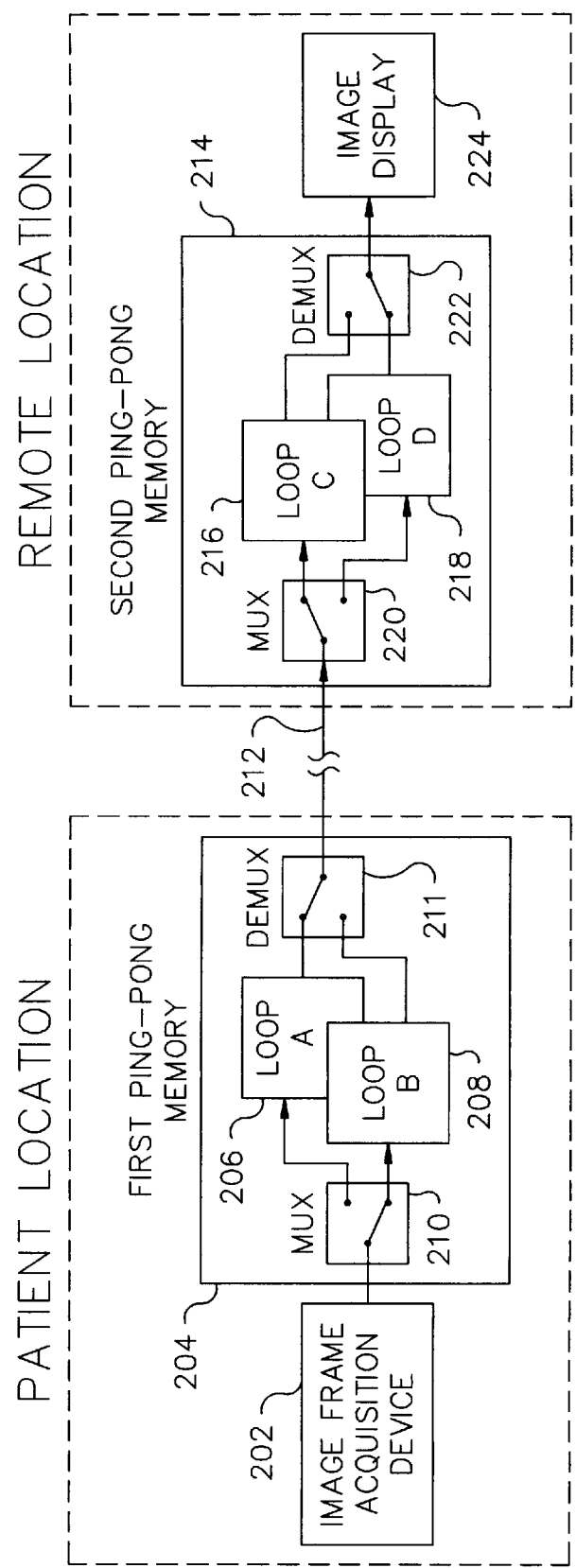
FIG. 28 is a schematic block diagram of a first system for implementing a pseudo real-time transmission scheme in accordance with the present invention.
Figure 29:
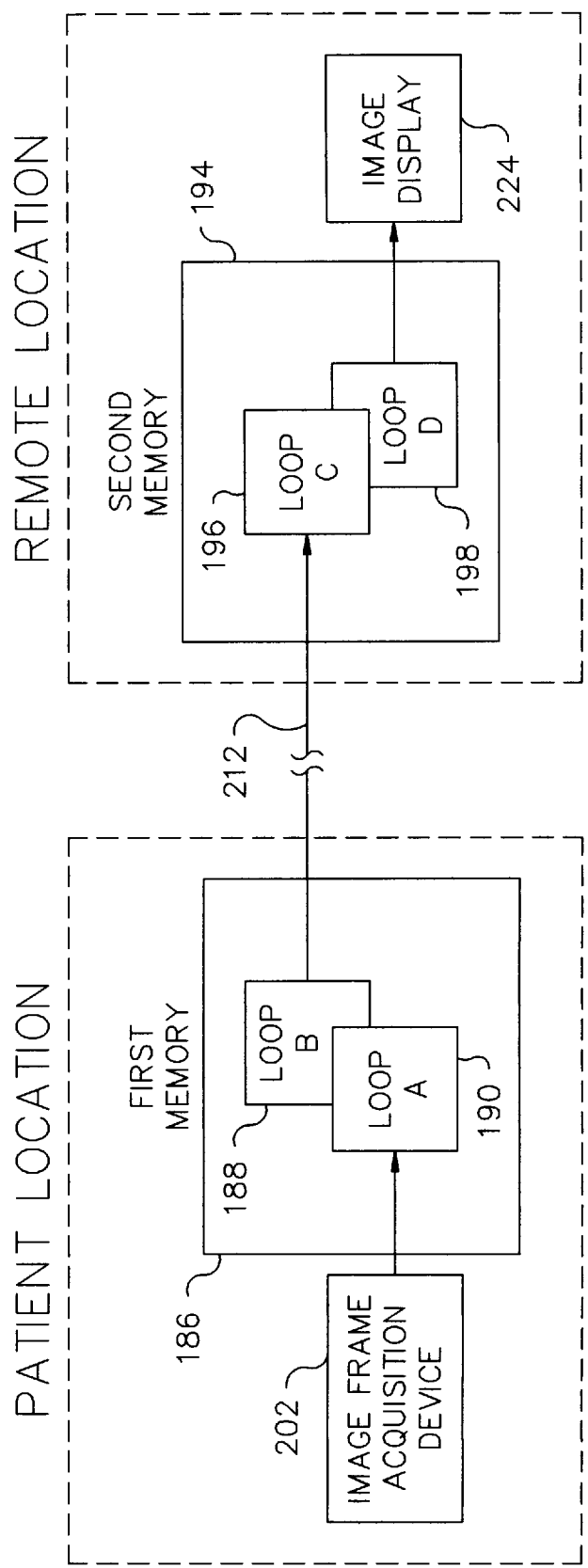
FIG. 29 is a schematic block diagram of a second system for implementing a pseudo real-time transmission scheme in accordance with the present invention.

One beneficial application of image loops 100 is in telemedicine, wherein the patient location 120 in FIG. 5 is rural or remote diagnostic site, and highly skilled specialists receive and analyze the data at the remote location 122. By packaging the image data into image loops 100, the communication process can be significantly simplified compared to the prior art. Furthermore, the image loops 100 can be easily transmitted using various communication media, such as the Internet. If the communication medium does not consistently support the full required bandwidth of the real-time data stream of image data, one preferred transmission scheme is to transmit the image loops 100 in pseudo real-time. Two suitable processes for implementing a pseudo real-time transmission scheme are shown in FIGS. 28 and 29, described below.

The image frame data stored in the image loops 100 may represent raw image data before it is processed by a scan converter, or the image frame data may represent display-type pixel data (i.e., raw image data which was processed by a scan converter).

The image loops 100 are also useful in implementing the remaining portions of the present invention, as discussed below. However, their use is optional in the other portions of the present invention.

Image Frame Rates and Image Frame Acquisition and Collection

In grayscale (gray-scale) ultrasound, a B-scan technique amplifies and processes the echoes according to their strength and creates a visual display ranging from white for the strongest echoes to varying shades of gray. The display may be referred to as a B-Mode display. The B-mode display presents a two-dimensional display that is updated periodically as determined by the frame rate. Data is typically acquired at the highest image frame rate necessary to fully capture the motion of the fastest moving structures presumed to be present. For a fast-moving structure such as the heart, an acquisition frame rate of more than 30 FPS must be used to accurately represent the motion during the fastest portion of the heart cycle. For a slow-moving structure such as the liver, a lower frame rate may be used, such as less than 15 FPS.

The acquisition frame rate is limited by the number of scan lines being obtained, the frequency of the ultrasound transmission signal, and the depth of the scan. The scan depth is an important factor in limiting the frame rate. A deeper depth will result in slower receipt of the echo signal, since the speed of sound introduces an inherent limit on the speed of the transmission and echo signals.

As discussed above, in cardiac imaging, the motion of tissue structure is normally periodic. Each period is known as a heart cycle and its length of time is determined by the heart rate. The rate of motion of the structure exposed to ultrasound waves varies at different times within the heart cycle. For example, the rate of motion during systole (i.e., the systolic portion of the cycle) is greater than the rate of motion during diastole (i.e., the diastolic portion of the cycle). Thus, it is not necessary to sample the heart at the same rate in both portions of the cycle to fully and sufficiently represent the imaged structure. A slower sampling rate may be used for the diastolic portion of the cycle.

Notwithstanding this fact, commercial ultrasound systems typically sample at a fixed frame rate throughout the entire cycle. The fixed frame rate may be selected automatically or manually. If the fixed frame rate is selected to be sufficient to accurately represent the motion during the fastest portion of the heart cycle, then the image will be oversampled during the slower portions of the cycle (e.g., the diastolic portion). If the fixed frame rate is selected to be somewhat less than the frame rate necessary to accurately represent the motion during the fastest portion of the heart cycle, then the image will sometimes be oversampled, and will sometimes be undersampled. Oversampling results in the acquisition of redundant (unnecessary) data, which must be stored and processed or transmitted. Undersampling results in the loss of potentially important image information. Commercial systems also typically collect the acquired image data at a fixed frame rate throughout the entire cycle for storage, display or review, or transmission to a remote site.

The present invention provides two different schemes for matching the frame rate more closely with the rate of motion of the anatomic structure. The first scheme matches the collection frame rate more closely with the rate of motion of the anatomic structure, and is described with respect to FIGS. 6–12. The second scheme matches the acquisition and collection frame rate more closely with the rate of motion of the anatomic structure, and is described with respect to FIGS. 15–18.

Adjustable Collection Image Frame Rate

The first scheme obtains and processes two types of ultrasound images, (1) collection image frames which are "collected" (i.e., captured and stored for immediate or subsequent display or review, and alternatively, for transmission to a remote site), and (2) interrogation image frames which are used to monitor activity in the time between acquisition of collection image frames, and which are not "collected." The interrogation image frames may be temporarily stored in a memory buffer, as described below. The first scheme uses a frame correlation procedure to determine if and/or when the anatomic structure is exhibiting movement, and adjusts the type of images which are acquired at subsequent time intervals in response to the amount of movement. The interrogation frames effectively sample the anatomic motion, and provide an early warning that the rate of motion is changing. If the rate of motion has changed, then an adjustment should be made to the number of collection image frames that are acquired and collected in a given time period.

FIG. 6 is a schematic block diagram of a medical ultrasound imaging system 132 for implementing the first scheme. The system 132 includes an image frame acquisition device 134, an image frame controller 136 (which may part of the acquisition device 134 or which may be separate from the acquisition device 134), an image processor 178, an image frame memory 138, a frame correlation processor 140, and an image display 142. The image frame acquisition device 134 includes a transducer probe 144 and a processor 146. The transducer probe 144 may be any suitable conventional probe containing a transmitter (not shown) for transmission of ultrasound energy into the subject's body, and a receiver (not shown) for receiving the resultant echoes. The output of the image frame acquisition device 134 is connected to the input of the image processor 178. The image processor 178 has a first output connected to a first input of the image frame memory 138 and to the image display 142 for passing unfiltered or temporally filtered collection image frames to the image frame memory 138 and to the image display 142. The image processor 178 also has a second output connected to a first input of the frame correlation processor 140 for passing collection image frames and interrogation image frames to the frame correlation processor 140. The image processor 178 has an optional third output connected to a second input of the image frame memory 138 for passing interrogation frames to the image frame memory 138. The image frame memory 138 may optionally be connected at its output to an input of the frame correlation processor 140 for passing selected interrogation frames to the frame correlation processor 140. The output of the frame correlation processor 140 is connected to the input of the image frame controller 136. The output of the image frame controller 136 is connected to an input of the processor 146.

The acquisition device 134 produces a series of image frames. Each image frame comprises data representing an image of a portion of the subject's body at a given time. In a first embodiment of the adjustable collection image frame rate scheme, the device 134 produces image frames of at least two different resolutions. The image frames at lower resolutions are acquired in less time than the image frames acquired at higher resolutions. For illustration purposes, the first embodiment of this scheme is described in the context of a dual resolution scheme wherein the collection image frames have a first resolution, and the interrogation image frames have a second resolution. Preferably, the collection image frames have a higher resolution than the interrogation frames. Image frames produced at the first (higher) resolution are interchangeably referred to herein as "full-resolution image frames" or "full-resolution frames" and preferably represent the maximum resolution of the acquisition device 134. Image frames produced at the second (lower) resolution are interchangeably referred to herein as "low resolution interrogation image frames" or "low resolution interrogation frames." The processor 146 of the acquisition device 132 thus outputs two different types of image frames, namely, full-resolution frames and low resolution interrogation frames. The processor 146 controls the transducer probe 144 to produce one or the other types of image frames, depending upon the signal that it receives from the image frame controller 136, as discussed in more detail below. The image frame memory 138 receives the full-resolution frames and stores them in a storage portion 148 of the frame memory 138. In the preferred embodiment of the present invention, the low resolution interrogation frames are not stored in the image frame memory 138, since only the current low resolution interrogation frame is needed for the preferred mode of operation. However, an alternative embodiment of the invention discussed below may use recently acquired low resolution interrogation frames, and thus a temporary storage portion 150 may be provided in the frame memory 138 for this purpose. The full-resolution image frames obtained from the output of the acquisition device 134 are communicated to the image display 142 for real-time monitoring of the image acquisition process. The image processor 178 includes a filter or switch 180 which blocks all interrogation image frames (regardless of their resolution) from being passed to the image display 142 or to the storage 138, and allows all collection image frames (e.g., full-resolution image frames) to pass therethrough. One suitable scheme for implementing the switch 180 is to use an image frame tagger in the processor 146 of the acquisition device 134 to tag or identify each acquired image frame as being either a collection image frame or an interrogation frame. If image data is acquired as image loops 100, the frame header 108 may be used to tag the type of image frame, as discussed above.

Figure 7A:
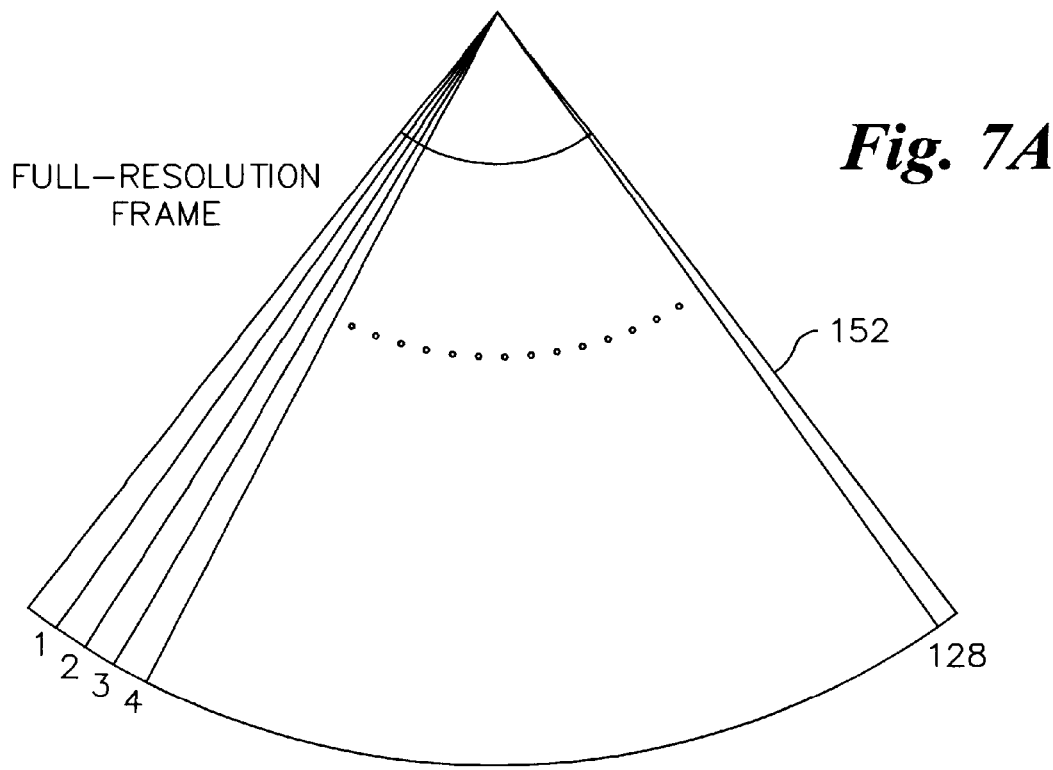
FIGS. 7A and 7B show two types of image frames which may be captured using the system of FIG. 6.

FIG. 7A shows a full-resolution frame 152 which contains the maximum possible number of ultrasound scan lines achievable by the particular equipment (128 in this example), and a low resolution interrogation frame 154 which samples only selected scan lines, such as every 4th scan line. The full-resolution frame 152 thus has a greater line density than the low resolution interrogation frame 154.

The general operation of the FIG. 6 imaging system 132 is as follows: Successively acquired image frames 152 or 154 are continuously compared using a conventional scheme (e.g., a pixel difference scheme) to determine the amount of difference between the successive images. The amount of difference is expressed as a "frame correlation coefficient." If there are a large number of differences (i.e., a low frame correlation coefficient), then the "effective frame rate" is set to a fast rate, or is maintained at a fast rate if already set to a fast rate. If there are a small number of differences (a high frame correlation coefficient), then the effective frame rate is reduced, or maintained at a reduced rate if already set to a reduced rate. The goal of the system 132 is to obtain and store as many full-resolution image frames 152 in a given time as is necessary to sufficiently capture important anatomic motion, while minimizing the amount of full-resolution image frames 152 which merely provide redundant information.

Figure 7B:
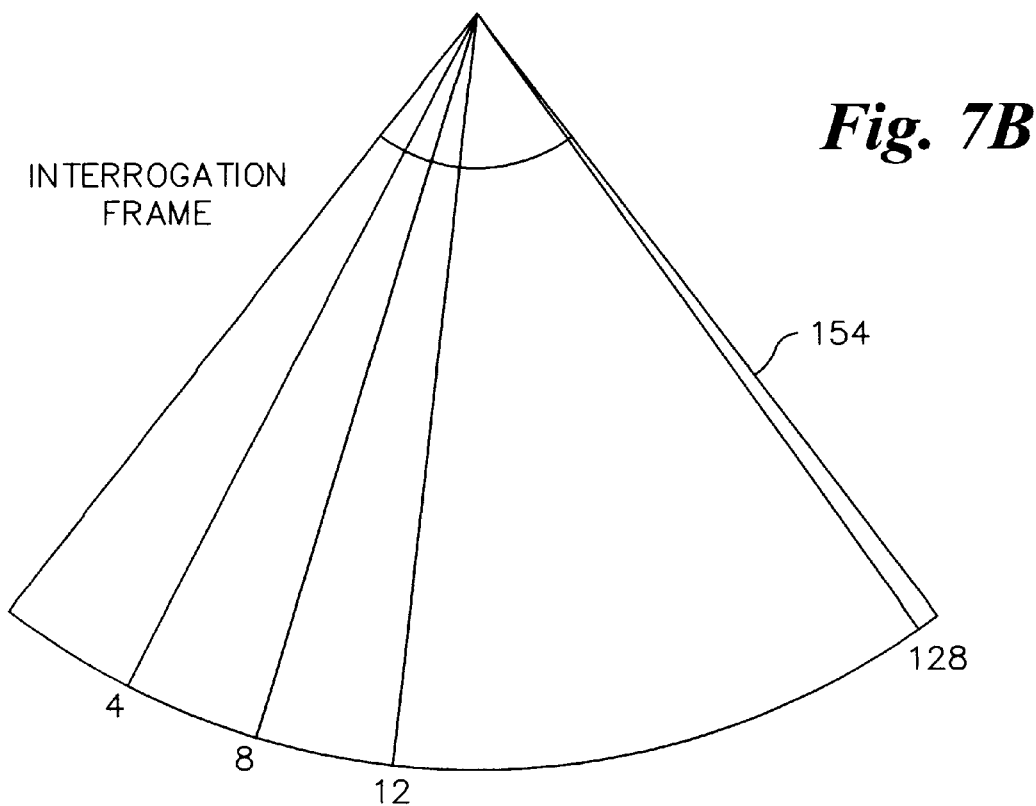

The "effective frame rate" is determined by how many full-resolution image frames are collected in a given period of time. Consider the example wherein maximum resolution is desired. In this case, no low resolution interrogation frames are obtained, and the entire imaging period is used to collect full-resolution images. The frame rate would thus be the maximum frame rate permissible by the equipment, such as 45 FPS. Next, consider the example wherein anatomic motion is very slow, and thus very little change from frame to frame. In this case, it may be acceptable to obtain only 15 FPS. During operation at a reduced frame rate, there is so-called "dead time" between capturing of successive full-resolution images 152. That is, there is a time period in which a full resolution sample could be taken based on the capabilities of the equipment, but is not taken, since the image data would be redundant and would result in unnecessary collected data. During this dead time, one or more low resolution interrogation frames 154 are obtained. The number of low resolution interrogation frames 154 taken between full resolution frames 152 depends upon the length of the dead time and the line density of the low resolution interrogation frame 154. Since a low resolution interrogation frame 154 has a significantly lower line density than a full-resolution frame 152, a plurality of low resolution interrogation frames 154 may be taken in the same time period that it would take to obtain one full-resolution frame 152. In the example of FIGS. 7A and 7B, four low resolution interrogation frames 154 can be obtained in the time period required to obtain one full-resolution frame 152, since the capture time is generally proportional to the number of scan lines.

To illustrate an actual data collection session, consider an example wherein the acquisition system 132 is currently collecting full-resolution frames 152 at less than the maximum rate, and low resolution interrogation frames 154 are being collected in the "dead time" between collection of the full-resolution frames 152. In this example, the low resolution interrogation frames 154 are processed in the following manner:

After each low resolution interrogation frame 154 is obtained, the frame correlation processor 140 determines the amount of difference between the current low resolution interrogation frame 154 and the last full-resolution frame 152. In the example of FIGS. 7A and 7B, the frame correlation processor 140 uses all of the scan lines of the low resolution interrogation frame 154 and every 4th corresponding scan line of the full-resolution frame 152. If there are a large number of differences between the current low resolution interrogation frame 154 and the sampled scan lines of the last full-resolution image 152 (i.e., a low frame correlation coefficient), then the image frame controller 136 increases the effective frame rate by causing more full-resolution images to be acquired in a given time period. That is, the FPS is increased, wherein "F" refers to a full-resolution frame 154. If there are no significant differences between the latest low resolution interrogation frame 154 and the last full resolution image 152 (i.e., a high frame rate correlation coefficient), then the frame rate is reduced, or is not changed if it is already at the lowest rate.

Consider next an example wherein the acquisition system 132 is currently collecting full-resolution frames 152 at the maximum rate, and no low resolution interrogation frames 154 are being collected, since there is no "dead time" between collection of the full-resolution frames 152. This condition is preferably used upon start-up of the equipment, since no information is available about the motion of the anatomic structure exposed to ultrasound waves. This condition may also occur at any time in the acquisition process if fast anatomic motion is detected. In this example, the full-resolution frames 152 are processed in the following manner:

After each full-resolution frame 152 is obtained, the frame correlation processor 140 determines the amount of difference between the current full-resolution frame 152 and the last full-resolution frame 152. If there are a large number of differences between the two frames 152 (i.e., a low frame correlation coefficient), then the image frame controller 136 maintains the frame rate at the current rate, and thus continues to collect only full-resolution frames 152. If there are no significant differences between the two frames 152 (i.e., a high frame rate correlation coefficient), then the full-resolution image frame rate is reduced, and the system 132 starts obtaining low resolution interrogation frames 154 in the dead time between collection of full-resolution frames 152.

In sum, the image frame controller 136 adjusts the collection image frame rate in inverse proportion to the most recent frame correlation coefficient. The resolution of the ultrasound image is determined by the number of scan lines per frame. Thus, to obtain the desired image frame rate, the acquisition device 134 produces the desired image resolution (as determined from the output signal of the image frame controller 136) by causing the transmitter of the transducer probe 144 to transmit the appropriate number of scan lines to obtain the desired resolution. In the example of FIG. 7A, the transducer probe 144 would transmit 128 scan lines to obtain the full-resolution frame 152, and would transmit 128/4 or 32 scan lines to obtain the low resolution interrogation frame 154. In one implementation of the acquisition process, the image frame controller 136 outputs a frame trigger signal to cause the acquisition device 134 to obtain a full-resolution image whenever it is deemed necessary based on the frame correlation results.

In the preferred embodiment of the present invention, each successively acquired low resolution interrogation frame 154 is compared to the last acquired full-resolution frame 152. However, in an alternative scheme, each low resolution interrogation frame 154 is compared to the previously acquired image frame, regardless of whether that image frame is a full-resolution image frame 152 or a low resolution interrogation frame 154. Thus, a succession of currently acquired low resolution interrogation frames 154 may be compared to previously acquired low resolution interrogation frames 154. This scheme is not preferred, because small changes between successive low resolution interrogation frames 154 may not trigger any change to the frame rate, when, in fact, the current low resolution interrogation frame 154 has become very different from the last acquired full-resolution image frame 152. To implement this alternative scheme, the temporary storage portion 150 of the image frame memory 138 is used to store and retrieve a previously acquired low resolution interrogation frame 154, when needed (i.e., whenever the last two acquired image frames are low resolution interrogation frames 154).

To ensure sufficient collection of full-resolution frames 152, the system 132 may be programmed to collect a full-resolution frame 152 at periodic time intervals, even if no instruction signal or trigger signal is received from the image frame controller 136 or other controlling device to do so. This may occur if the frame correlation processor 140 detects no change from image to image, and the image frame controller 136 sets the effective frame rate to a very low rate. Periodic collection of full-resolution image frames 152 may be desirable for system integrity, even though the additional full-resolution image frames 152 may be redundant.

Figures 8, 10A, 10B, 11:
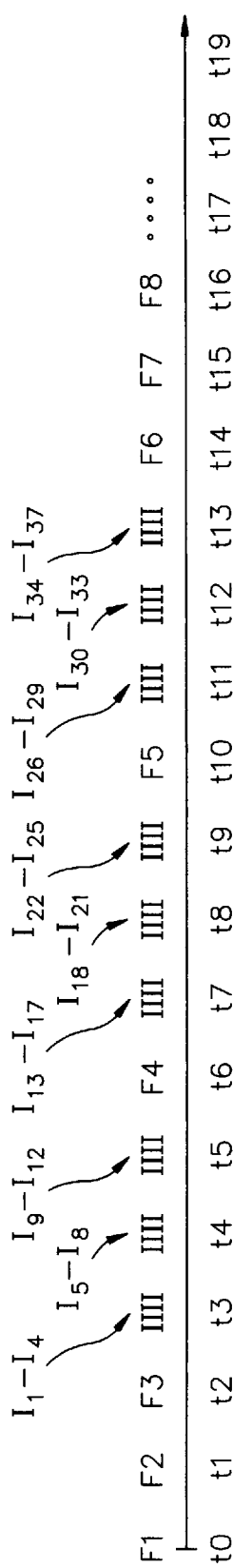
FIG. 8 illustrates a sample data acquisition session when using the system of FIG. 6.
FIGS. 10A and 10B illustrate imaginary brightness data for a four pixel portion of an image frame.
FIG. 11 is a table of mean difference values and associated frame rates for use with the system of FIG. 6.

FIG. 8 illustrates a sample data acquisition session. At start-up, full-resolution images are obtained. The samples F2 and F3 taken at times t1 and t2 show very high correlation, indicating that the frame rate can be significantly lowered, while still capturing sufficient information. In this example, the frame rate is lowered to obtain one full resolution sample every 4th time period. Interrogation frames are taken during the dead time (t3–t5). The interrogation frames I1–I4 are actually taken during the dead time between t2 and t3, the interrogation frames I5–I9 are actually taken during the dead time between t3 and t4, and so on. However, the interrogation frames are bunched together to simplify the illustration. In this example, a comparison of the interrogation frames I1–I12 obtained during the dead time (t3–t5) with full-resolution frame F3 indicate that no change should be made to the frame rate of once every 4th time period. Thus, this frame rate continues unchanged. Likewise, a comparison of the interrogation frames I13–I25 obtained during the dead time (t7–t9) with full-resolution frame F4 indicate that no change should be made to the frame rate of once every 4th time period. Thus, this frame rate continues unchanged. Toward the very end of the next dead time (t11–t13), the last one or two interrogation frames show very low correlation with the last acquired full-resolution image F5, meaning that the anatomic structure is now moving faster. As a result, the frame rate is increased to the original maximum rate.

Figure 9:
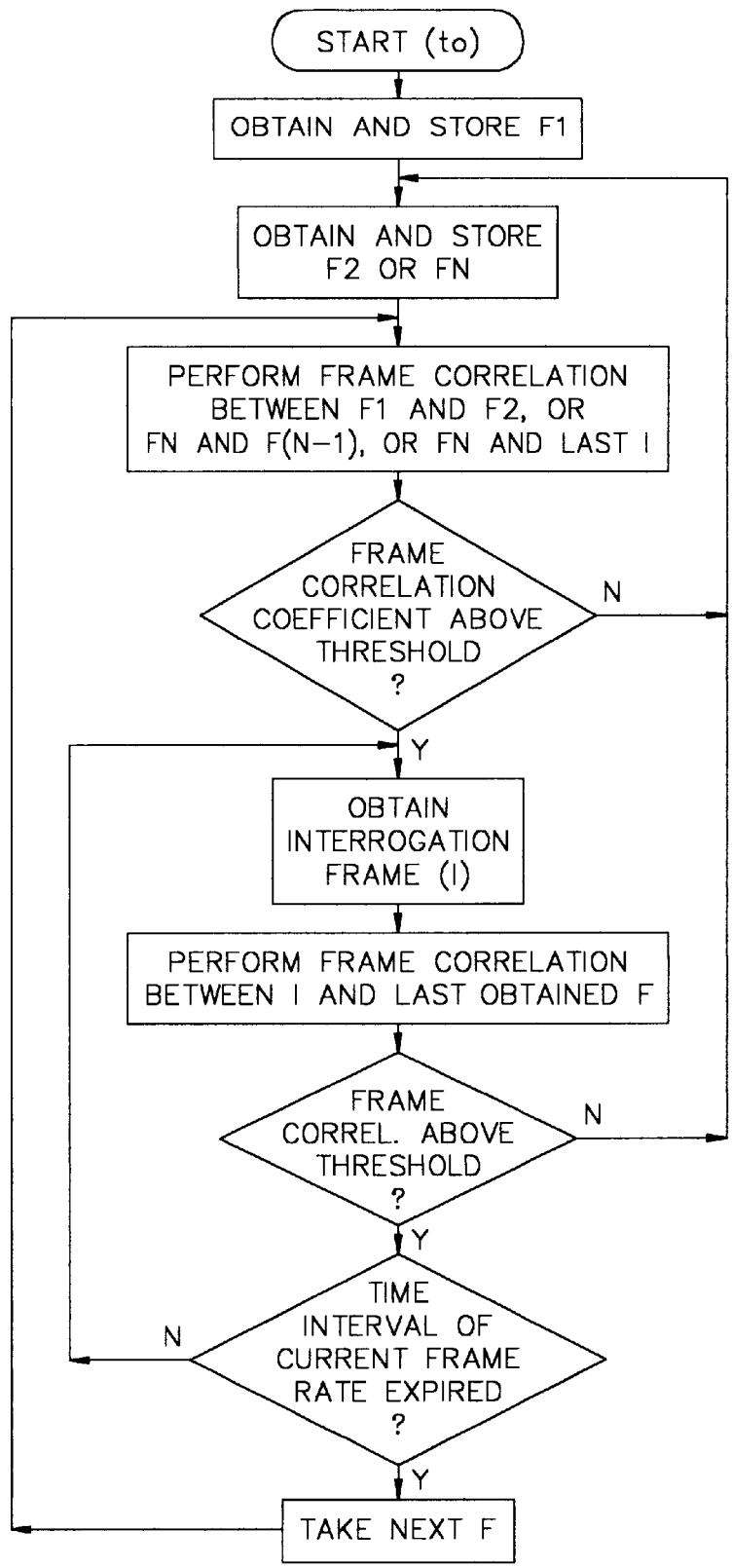
FIG. 9 is a flowchart of the process for acquiring data when using the system of FIG. 6.

FIG. 9 shows a self-explanatory function-type flowchart of the process described above.

The scheme illustrated in FIG. 8 has two different frame rates, namely, a first (fast) frame rate of one full-resolution frame per time period, and a second (slow) frame rate of one full-resolution frame per four time periods. One suitable two-speed embodiment may have a fast frame rate of about 40 FPS (one full-resolution frame 152 is collected about every 25 ms), and a slow frame rate from about 10 FPS to a frame rate of about 30 FPS (one full-resolution frame 152 is collected about every 100 ms to about every 33 ms). The scope of the invention also includes schemes having more than two different frame rates.

FIGS. 10A and 10B illustrate the concept of frame correlation and show, in very simplified terms, the function of the frame correlation processor 140. Consider imaginary image frame data after processing by a conventional scan converter. To simplify the illustration, the imaginary image frame has only four pixels. The pixel values represent relative brightness levels from 0 to 9.

In FIG. 10A, image frame F1 and F2 from FIG. 8 differ only slightly in the upper right pixel, and thus are highly correlated. The mean difference of the two image frames (i.e., the difference between each corresponding pixel divided by the number of pixels) is 1.0/4=0.25. In FIG. 10B, image frames F5 and I37 differ significantly and thus have a low frame correlation coefficient. The mean difference of the image frames of FIG. 10B is ((7–2)+(5–1)+(4–3))/4= 2.5. The mean difference may be expressed mathematically as:

$$\text{mean difference} = \text{avg}\{\text{abs}\{f(n) - f(n-1)\}\} \text{ or}$$

$$\sum_{pixels} |f_i(n) - f_i(n-1)| / \text{\# of pixels}$$

wherein f(n) is the current image frame and f(n–1) is the previous image frame.

To reduce the effect of noise on the mean difference calculation, a low level threshold may be applied to the image frames to remove all pixels below a chosen intensity level.

As further background to the frame correlation process, see U.S. Pat. No. 5,060,515 (Kanda et al.), incorporated in its entirety herein by reference.

FIG. 11 shows one method of using the mean differences for setting the collection image frame rate. The image frame controller 136 may include a table of mean differences and collection image frame rates associated with each mean difference. In the two frame rate (fast and slow) embodiment, a threshold mean difference is used to set the frame rate. If more than two frame rates are used, then different ranges of mean differences may correlate to different respective frame rates. The values shown in FIG. 11 are for illustration purposes, and do not represent values associated with an embodiment of the present invention. Suitable normalized mean difference thresholds for a three frame rate embodiment, based on experimental data wherein relative brightness levels of pixels range from 0 to 127, are as follows:

| Mean difference | Frame Rate (3 rates) |
|---|---|
| 6–7 | SLOW |
| 8–9 | MEDIUM |
| 10–11 | FAST |

For a two frame rate embodiment, the SLOW frame rate may be used for normalized values less than 9 or less than 10, and the FAST frame rate may be used for values greater than or equal to 9, or greater than or equal to 10.

FIG. 12 shows one preferred scheme for storing the time interval between adjacent (successively acquired) full-resolution image frames 152. The time interval thus effectively represents the instantaneous collection image frame rate. During playback, this information is used to determine how long the image frame 152 should persist on the display screen before being replaced by the next image frame 152. The time intervals shown in FIG. 12 are represented in number of time periods, and match the image frames 152 of FIG. 8. When the image frames 152 are stored within image loops 100, the time between adjacent frames may be stored as part of the frame header 108, as discussed above.

The acquisition device 134 preferably operates by setting the effective collection image frame rate based on the input from the image frame controller 136, and then automatically acquiring interrogation frames 154 during dead times. The interrogation frames 154 are preferably acquired at the fastest rate possible to maximize usage of the dead time. The number of interrogation frames 154 that can be acquired in the dead time depends upon its resolution (i.e., scan line density). The 4:1 ratio example of FIGS. 7A and 7B provides an acceptable compromise between resolution and number of interrogation frame samples 154 obtainable during the dead times. However, other resolutions are within the scope of the invention. For example, a 2:1 ratio would be feasible, and would constitute a significant difference in resolution. If the interrogation frame 154 has a scan line density similar to a full-resolution image 152, system performance would be degraded because the number of interrogation frames 154 that can be acquired during the "dead time" would be very low (such as one or so), and thus very little sampling would occur during the dead time. This would cause a delay in any frame rate change, resulting in either loss of important image data or collection of unnecessary image data. However, other advantages are possible if the resolutions of the two types of image frames are similar, as discussed immediately below.

In a second embodiment of the adjustable collection image frame rate scheme, the resolution of the collection image frame is either the same or lower than the resolution of the interrogation image frame. In the preferred second embodiment, the resolutions of the two images are the same. The implementation of this embodiment is generally similar to the first embodiment, except for the following differences:

(1) The number of scan lines in the two types of image frames shown in FIGS. 7A and 7B are identical. This simplifies the scanning electronics, allowing a conventional acquisition device to be easily retrofitted for use as the acquisition device 134 in FIG. 6. The only significant modification required to a conventional acquisition device is that each image frame must be tagged or otherwise identified as being either a collection image frame or an interrogation image frame, so that the succession of image frames output from the acquisition device 134 may be processed, filtered and collected in the same manner as in the first embodiment. For example, the interrogation image frames must be identified so that they are not "collected." Since the resolutions of the two types of image frames are the same, the acquisition image frame rate remains constant, whereas the collection image frame rate changes depending upon the latest output of the frame correlation processor 140.

(2) Since the scan lines of the two types of image frames are identical, only one interrogation frame is collected in each time period. Thus, in FIG. 8, only one interrogation frame is collected in time periods t3–t5, t7–t9, t11–t3, and so on. As noted above, this difference degrades system performance.

The reduced system performance can be somewhat improved by using an optional conventional temporal filter 182 inside the image processor 178 to temporally filter the collection image frames with one or more adjacent interrogation frames. The total number and time periods of the collection image frames would be the same as in a scheme without temporal filtering. However, the collection image frames may be higher in quality (e.g., reduced noise) than if the frames were passed through unfiltered.

The second embodiment provides the same advantages as the first embodiment in reducing the volume of image data that must be collected while providing an adjustable collection image frame rate scheme which improves performance over conventional acquisition systems which acquire and collect image frames at a fixed frame rate.

Many alternative embodiments are within the scope of the invention. For example, the frame correlation processor 140 may use more than one previous image frame to determine the correlation coefficient, and different weightings may be applied to the image frames. These techniques are well known and thus are not described in further detail herein.

Unlike the example of FIG. 8, the system 132 may be designed to always collect interrogation frames 154 between full-resolution frames 152, even at the fastest frame rate setting. However, the number of interrogation frames 154 taken between full-resolution frames 152 would vary according to the frame rate. Furthermore, the resolution of the interrogation frames 154 may be varied for selected dead times, or within each dead time.

An interrogation frame could have a scan line density similar to a full resolution image. However, this would degrade system performance because the number of interrogation frames that can be collected during the "dead time" would be reduced, and thus less sampling would occur during the dead time. This would cause a delay in the frame rate change, resulting in either loss of important image data or collection of unnecessary image data.

Use of Frame Correlation Processor to Locate a Predetermined Event in a Physiologic Cycle The output of the frame correlation processor 140 may be used to locate a predetermined event in a physiologic cycle, such as the time interval associated with a QRS trigger in a heart cycle. Thus, image frames may be used to selectively replace physiological monitoring equipment in certain applications.

FIG. 13 is a schematic block diagram of an imaging system 156 which may be used to replace a physiological monitor. FIG. 13 is described in the context of a QRS trigger detection device, although the system 156 may be used for detecting points in other types of physiologic cycles which are characterized by motion changes. The system 156 includes the same image frame acquisition device 134, image frame memory 138 and frame correlation processor 140 described above. The frame correlation processor 140 receives a stream of successively acquired image frames, consisting of collection image frames, such as full-resolution frames 152, or combinations of collection image frames and interrogation frames. The frame correlation processor 140 determines the difference between the current image frame and at least one preceding image frame and outputs a frame correlation coefficient based upon the difference, in the same manner as described above. The correlation coefficients output from the frame correlation processor 140 are input to a QRS trigger detector 158 which determines the QRS trigger therefrom. The time interval associated with the QRS trigger is identified as the instance of time when the frame correlation coefficient falls below a predetermined value, or instance of time when the rate of change of the frame correlation coefficient becomes greater than a predetermined value.

FIG. 14A is a graph of a portion of a heart cycle shortly before, during, and shortly after systole which indicates relative motion of the heart being imaged. FIG. 14A also shows corresponding frame correlation coefficients obtained in this region of the heart cycle. As relative motion increases, the frame correlation coefficient decreases, and vice-versa. The frame correlation coefficients are relatively high and stable, until the onset of systole when they begin to decrease. Likewise, the frame correlation coefficients are relatively low during systole, and begin to rise again as systole ends. The QRS trigger may be located by detecting when the frame correlation coefficients begin to decline, since the QRS trigger is associated with the onset of systole. Additional heart cycles may be used to improve detection accuracy. The QRS trigger may be used to calculate the heart rate, or to control conventional acquisition equipment which currently requires a QRS trigger obtained from a conventional physiological monitor. The QRS trigger detector 158 may use the mean difference values instead of the frame correlation coefficients.

FIG. 14B shows corresponding mean first difference values obtained from experimental heart image data for one complete heart cycle. These values correspond to calculations based on pixels having relative brightness levels ranging from 0 to 127. These experimental values also illustrate how the mean difference values discussed above for the experimental data of actual measured pixels may be used to select the appropriate frame rate. Referring to FIG. 14B, the mean difference values at the start of systole reach a peak of 10, thereby providing a readily identifiable indicator of this stage in the heart cycle.

Adjustable Acquisition Image Frame Rate

The present invention also provides a second scheme for matching the acquisition and collection image frame rates more closely with the resolution needs of the underlying structure. The acquisition and collection image frame rates are the same in this scheme, and are referred to hereafter as "the frame rate." The frame rate is set based on the expected rate of tissue motion. The second scheme also uses the acquisition device 134 and the image frame controller 136 of the first scheme. However, the second scheme does not perform frame correlation and does not collect interrogation frames. Instead, a physiological monitor monitors a cyclical physiological parameter associated with a physiologic cycle, and detects a predetermined event in the physiologic cycle. The image frame controller 136 functions as a frame rate controller to select the frame rate based upon the current point in time of the physiologic cycle with respect to the detected event. The frame rate may also be varied based upon the latest measurement of the total time of the physiologic cycle. This scheme thus estimates or predicts the expected rate of tissue motion during each phase of the cycle and sets the frame rate based on the expected rate of tissue motion.

Consider the example wherein the physiologic cycle is the heart cycle, the cyclical physiological parameter is an electrocardiogram and the detected event is the QRS trigger in the heart cycle. In this example, image frame controller 136 receives a signal from an EKG monitor, determines the predetermined points in time of the heart cycle relative to the QRS trigger, and sets the frame rate with respect to the current point in time. The frame rate may also be adjusted if the heart rate changes during the image acquisition session. For example, if the heart rate becomes very fast, such as during a treadmill stress test, the frame rate should be increased for all points in time in the heart cycle, to ensure that sufficient image data is collected.

Figure 15:
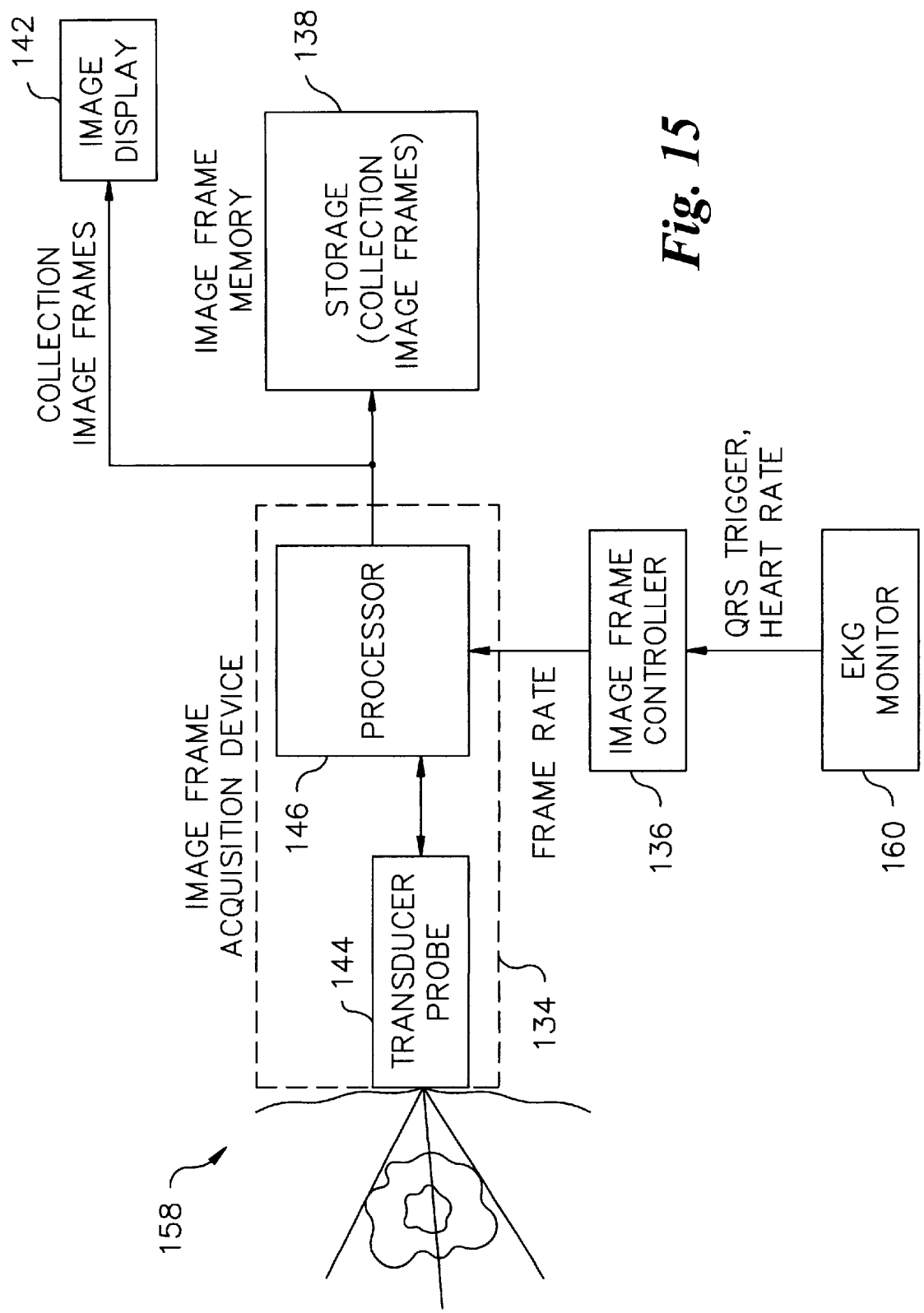
FIG. 15 is a schematic block diagram of a medical ultrasound imaging system in accordance with the present invention which has an adjustable acquisition image frame rate.

FIG. 15 is a schematic block diagram of a sample system 158 for implementing the second scheme. The system 158 is similar to the system 132 of FIG. 6, except that the image frame controller 136 receives a signal from EKG monitor 160, instead of from the frame correlation processor 140.

Figures 16, 17, 18:
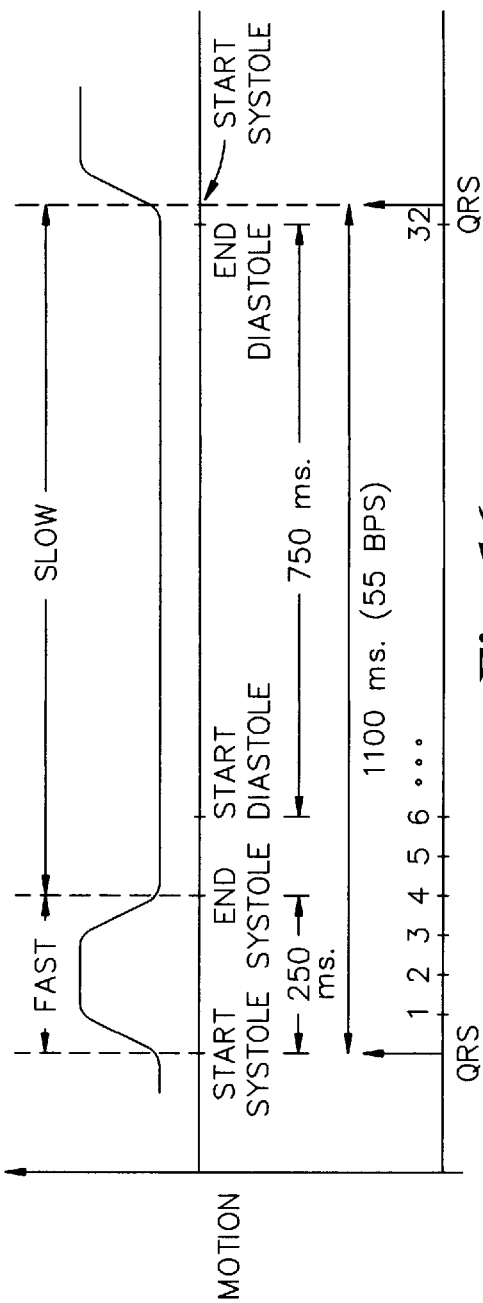
FIG. 16 is a graph of heart motion vs. time throughout the heart cycle.
FIG. 17 is a table of frame rates for different heart cycle intervals for use with the system of FIG. 15.
FIG. 18 is another table that may be used in conjunction with the table of FIG. 17 to determine the frame rate of the system in FIG. 15 based on the patient's heart rate.

FIG. 16 shows a graph of heart motion vs. time throughout the heart cycle, as well as a two-frame rate scheme implemented by the system 158. The heart rate in FIG. 16 is about 55 beats per minute (BPM). A fast frame rate is used during systole where a large amount of motion occurs. A slow frame rate is used during the remaining portions of the heart cycle, including during diastole where less motion occurs than during systole. Normative patient data may be used to predict the approximate start and end points of systole and diastole relative to the QRS trigger for the current patient. Alternatively, EKG data may be used to determine the exact location of such points for the current patient.

FIG. 17 shows a more sophisticated scheme wherein the heart cycle is divided into a plurality of intervals or segments, such as 32 intervals, and a frame rate lookup table is used to select the desired frame rate for the current portion of the cycle. The QRS trigger may be used to track the location in the cycle. Again, assumptions are made for a particular individual based on population data of motion rates at different times between QRS triggers. To create the table of FIG. 17, QRS triggers from a plurality of heart cycles are obtained. Next, the heart cycles are averaged to obtain an average cycle time. The average cycle time is then divided into evenly spaced time intervals. The time intervals are dynamically adjusted if the heart rate changes. The time intervals may also be used in the two frame rate embodiment. For example, intervals 1–7 may be the fast rate, and intervals 8–32 may be the slow rate.

FIG. 18 shows another table that may be used to determine the frame rate based on the heart rate, in conjunction with the table of FIG. 17. An average heart rate may be assigned a multiplier factor of 1.0. The multiplier factor would otherwise be proportional to heart rates which are above or below an average heart rate. The values shown in FIG. 18 merely illustrate the concept of adjusting the frame rate, in part, based on the heart rate, and do not represent preferred values. Actual values depend upon the amount of image data that the operator wishes to obtain.

In acquiring data using the second scheme, the time interval between adjacent image frames 152 is stored, in the same manner as the first scheme. Likewise, the time information may be stored in the frame loop header when packaging the image frames 152 in image loops 100.

Filtering Across Physiologic Cycles (Cycle-to-Cycle Filtering)

Ultrasound images are noisy. Noise is often the result of acoustic "speckle." Acoustic speckle is caused by interference patterns from wavefronts. The interference patterns cause constructive or destructive interference. Acoustic speckle shows up as bright spots and black holes on the image. One conventional technique for reducing acoustic speckle is to perform frame-to-frame "temporal filtering" (i.e., filtering in time).

Figure 19:
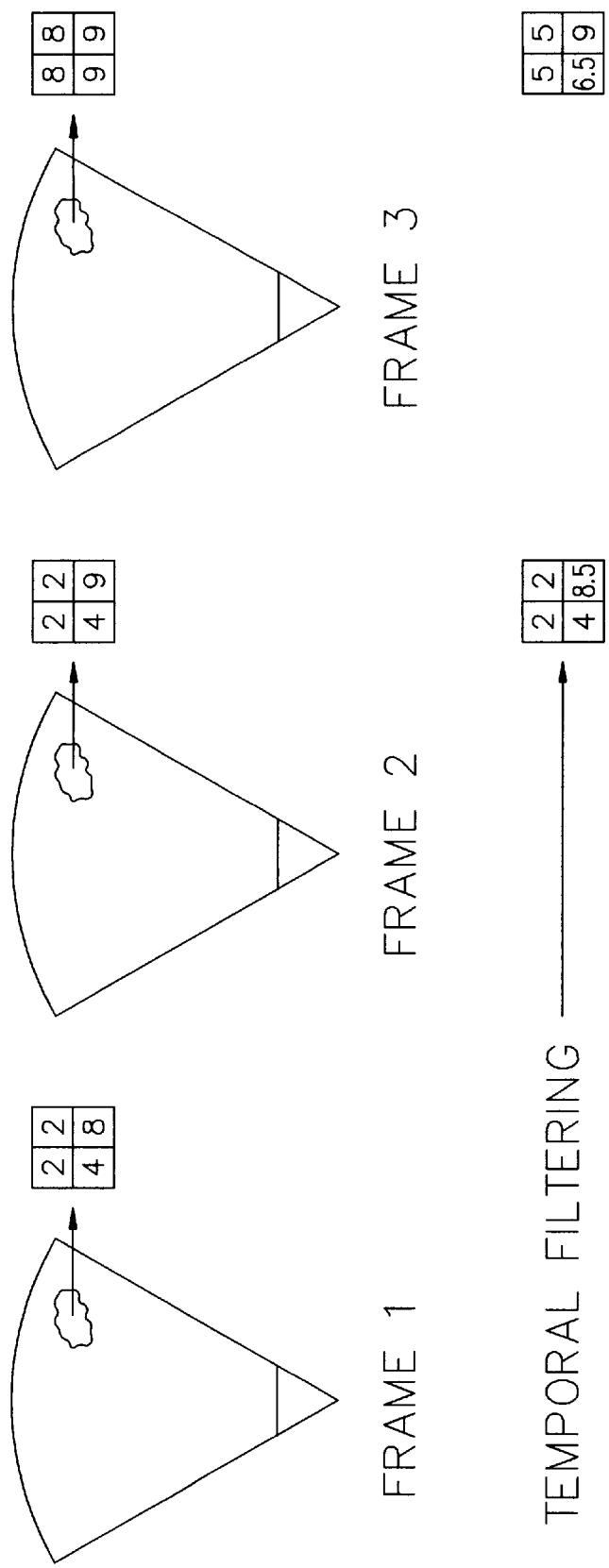
FIG. 19 illustrates a conventional temporal filtering scheme.

FIG. 19 illustrates a simple frame-to-frame temporal filtering scheme, as applied to a four-pixel region of an ultrasound image wherein each pixel is represented as a brightness number from 1–9. In this scheme, the pixels of the current frame are modified to be the average of the current pixel values and the pixel values of the previous image frame. The filter thus may be expressed as follows:

$$y(n)=\tfrac{1}{2}x(n)+\tfrac{1}{2}x(n-1)$$

wherein x(n) is the current frame and x(n−1) is the previous frame. Thus, the frame 2 and 3 pixels are modified as shown. If an anatomical object is moving slowly, this technique may be adequate in reducing speckle, without affecting the quality of the acquired data. For example, the image is moving slowly between frames 1 and 2 in the region of interest, since only one pixel changed, and only by one brightness level. However, if the anatomical object is moving fast, this technique reduces speckle, but also degrades the image, resulting in an image that does not accurately represent the actual state. For example, the image is moving fast between frames 2 and 3, since all of the pixels changed, and by large amounts. The resultant pixel numbers do not accurately represent the actual image and the resultant image becomes blurred.

The large change in pixel values does not indicate, per se, that the image is moving fast. Rather, it is an indication that the image at the time of capture of frame 3 is very different from the image at the time of capture of frame 2, and thus it can be inferred that this resulted from a quick movement in the anatomic structure.

Sophisticated temporal filtering techniques may use three or more frames and/or variable weightings and may filter recursively, but still suffer from the problem illustrated in FIG. 19.

To more effectively filter out noise from fast moving anatomic structures which exhibit periodic physiologic motion, the present invention applies the temporal filter across a sequence of physiologic cycles, instead of frame-to-frame. A physiologic cycle is divided into discrete time periods, and corresponding time periods from cycle to cycle are filtered. If the scheme of the present invention is applied to the heart, the QRS trigger may be used as the starting point of each heart cycle.

Conventional ultrasound systems may be used to perform contrast agent imaging and quantification in echocardiography. In one conventional technique, the QRS trigger is used as a reference point for obtaining a single pre-contrast image and a single post-contrast image at a predetermined point of interest in the cardiac cycle. The two images are then compared or subtracted from each other. To reduce any speckle associated with the pre-contrast and post-contrast images, some conventional systems obtain a plurality of pre-contrast and post-contrast images at the exact same point in successive cardiac cycles. Again, the QRS trigger is used as a reference point for identifying when the image for each cycle should be captured. The plurality of pre-contrast and post-contrast images are then separately filtered using a conventional filtering technique, such as averaging a plurality of such images. The result is a speckle-reduced pre-contrast image and a speckle-reduced post-contrast image obtained at a single point in the cardiac cycle. The resultant filtered images are then compared or subtracted from each other. This conventional technique is referred to herein as "single image cycle-to-cycle filtering." This technique does not provide image frames of the entire current physiologic cycle for full motion analysis of the cardiac cycle. That is, this conventional technique provides a filtered static image at only one point in the cardiac cycle. Thus, full motion analysis of the cardiac cycle cannot be performed using this conventional technique. The scheme of the present invention provides full-motion speckle-reduced image data.

Figure 20:
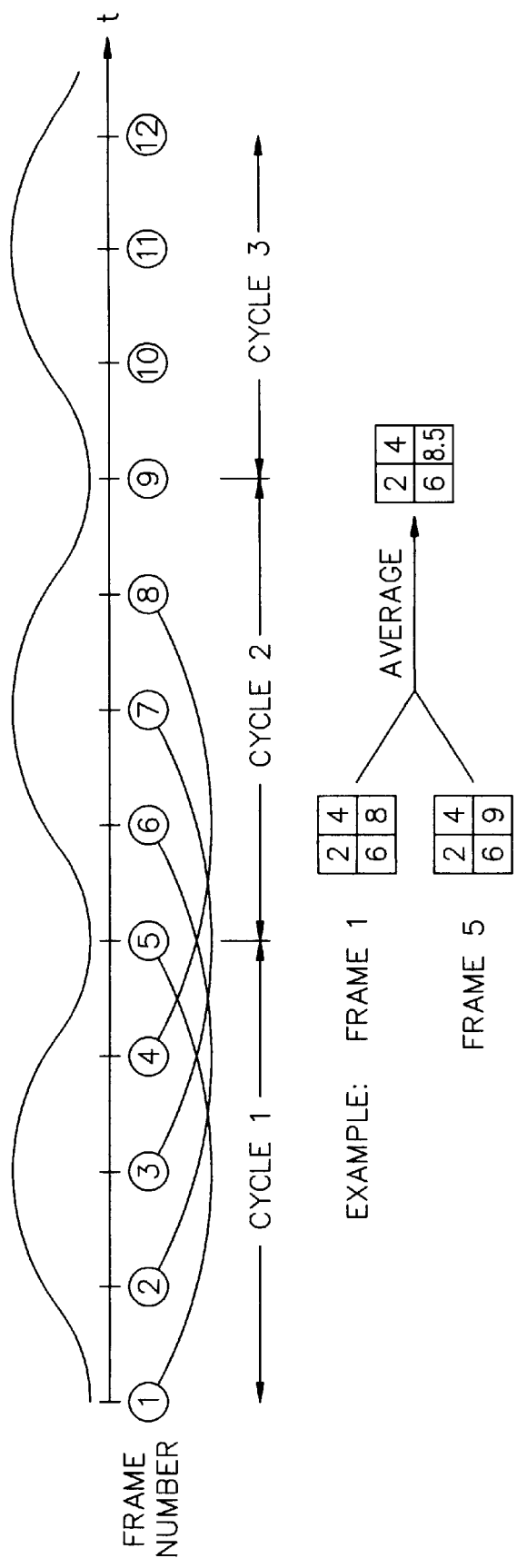
FIG. 20 illustrates a scheme for filtering ultrasound imaging data across physiologic cycles (i.e., cycle to cycle), in accordance with the present invention.

FIG. 20 shows a simplified scheme wherein adjacent time periods for adjacent cycles are filtered in the same manner as in FIG. 19 (that is, by averaging pixel brightness values for adjacent frames). In this scheme, four image frames are taken during each periodic physiologic cycle, such as the heart cycle. In a simple temporal (frame-to-frame) filtering scheme, frames 1 and 2, 2 and 3, 3 and 4, and so on, would be filtered. However, in the scheme of the present invention, filtering is performed at the same point in each cycle, on a cycle-to-cycle basis or "across" the physiologic cycle. Image (frame) acquisition is continuously resynchronized to the QRS trigger event. Any frame that had been in progress when the trigger occurs is discarded and a new frame is begun. Thus, filtering is performed on the frames obtained at the following time periods:

FRAMES 1 and 5 (see example of four pixel region in FIG. 20)
FRAMES 2 and 6
FRAMES 3 and 7
FRAMES 4 and 8
FRAMES 5 and 9
FRAMES 6 and 10
FRAMES 7 and 11
FRAMES 8 and 12
etc. . . .

This scheme uses a simple filter function having the formula set forth above in the example of temporal filtering. A more complex scheme which uses three frames would work as follows:

FRAMES 1, 5 and 9
FRAMES 2, 6 and 10
FRAMES 3, 7 and 11
FRAMES 4, 8 and 12 etc. . . .

This scheme is particularly effective for ultrasonic cardiac imaging in reducing speckle while minimizing spatial blurring.

The scheme is effective because the pixel values at the same point in two adjacent physiologic cycles are not likely to vary greatly whether the anatomic structure is moving fast or slow, since the anatomic structure should look very similar at the same points in adjacent physiologic cycles. This is especially true for fast-moving structure such as the heart. Thus the problem exhibited in FIG. 9 between frames 2 and 3 is less likely to occur.

Notwithstanding the simple filtering schemes described above which illustrate the inventive concept, the preferred filter is an nth-order infinite impulse response (IIR) filter. One significant advantage of such a filter is that it simplifies the image frame memory structure. For example, in a first order infinite impulse filter, only one image frame needs to be stored for each point in the cycle. A generalized IIR filter function is as follows:

$$y(n) = b_0 x(n) + b_1 x(n-1) + \ldots b_N x(n-N) + a_1 y(n-1) + a_2 y(n-2) + \ldots a_M y(n-M)$$

Figure 21:
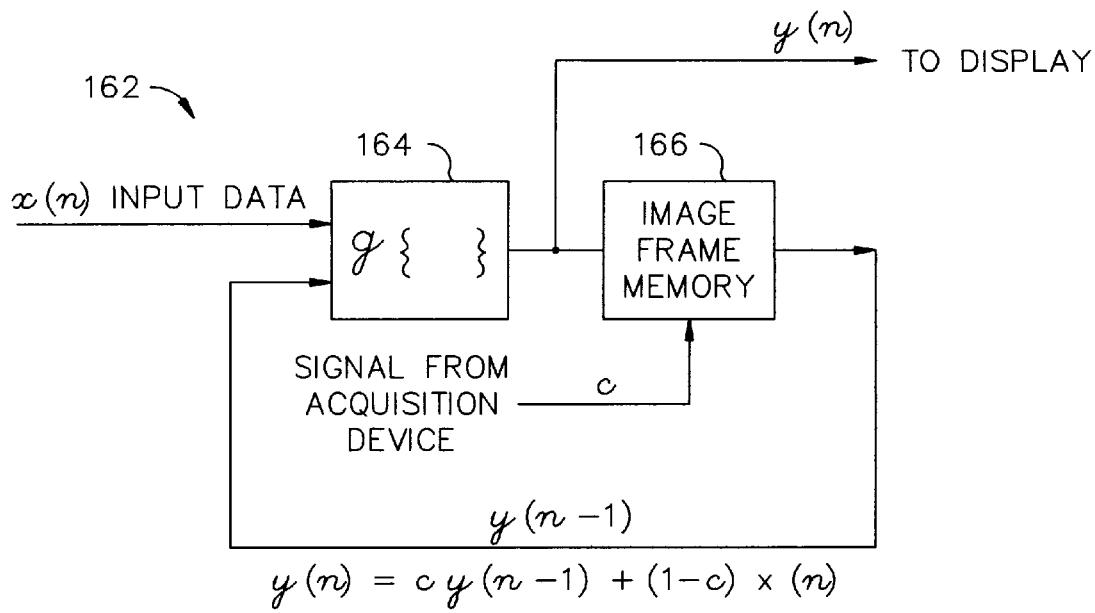
FIG. 21 is a schematic block diagram of a filter suitable for implementing the cycle to cycle filtering scheme of the present invention.

FIG. 21 is a schematic block diagram of a first order IIR filter 162 suitable for implementing the cycle to cycle filtering scheme of the present invention. The filter 162 includes a filter function block 164 and an image frame memory 166. The output of the filter function block 164 is connected to the input of the image frame memory 166 and to an image frame display (not shown). The filter function block 164 has a first input for receiving image frame data x(n) from an image frame acquisition device (not shown), and a second input for receiving image frame data y(n−1) stored in the image frame memory 166. Thus, there is a feedback loop between the filter function block 164 and the image frame memory 166. The filter 162 has the following function:

$$y(n) = c\, y(n-1) + (1-c)\, x(n)$$

wherein "c" is a constant which is less than 1

The value of the constant "c" determines how much of the past frames history is used in filtering the current frame. The greater the value of "c," the more history is used. If c=0, then y(n)=x(n). Thus, no history is used, and no filtering occurs. The constant "c" is set to zero whenever it is desired to pass through the current frame, such as when the filter must be reset, as discussed in more detail below. The value of "c" is set by an image frame acquisition device (not shown).

Figure 22:
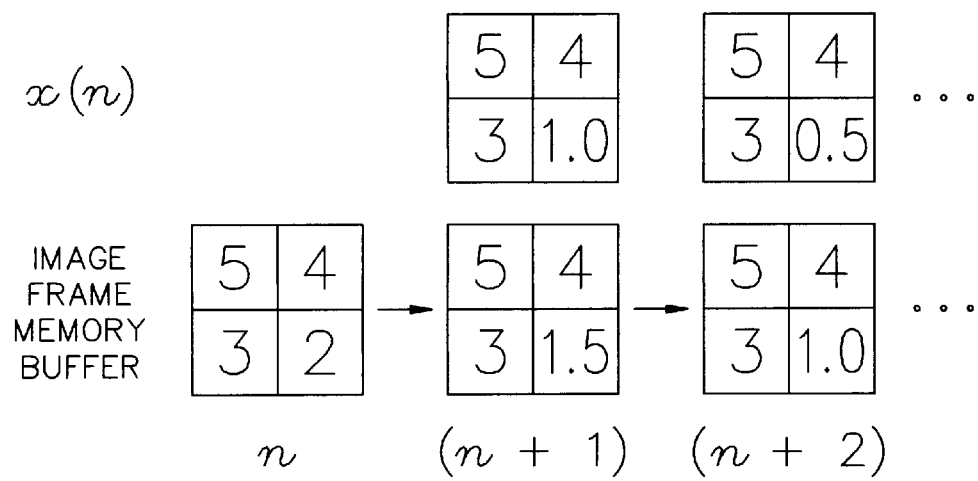
FIG. 22 shows how a four pixel region is filtered in accordance with the cycle to cycle filtering scheme.

FIG. 22 shows an example of how the IIR filter 162 processes a four-pixel region when c=0.5. The top line in FIG. 22 shows the new, incoming image data x(n) at times n+1 and n+2. The bottom line in FIG. 22 shows the contents of the image frame memory buffer of memory 166 at times n, n+1 and n+2. The image data represents the data at the same point in the physiologic cycle. Thus, n+1 is not the next acquired image frame, as would be the case in a temporal filter, but is the image frame of the next cycle at the same point in the cycle as the image frame n. Thus, in the simplified example of FIG. 20, there would be four different memory buffers in memory 166.

Referring to FIG. 22, at time n, the lower right pixel of the frame in the memory buffer is 2. At time n+1, the corresponding pixel of the new frame is 1. Since c=0.5, the two values are averaged, and the resultant new lower right pixel at time n+1 becomes 1.5. At time n+2, the corresponding pixel of the next new frame is 0.5. Again, the new pixel value is averaged with the latest pixel value in the memory buffer (now 1.5), and the resultant new value in the memory buffer becomes 1.0.

A number of different conditions may require that the constant "c" be set to zero so as to reset the frame memory 166. When the frame memory 166 is reset, the current frame becomes the new frame in the memory buffer, and the frame history information is lost. After resetting, the filtering process is restarted by returning the constant "c" to the previously set value. One condition that may require resetting is if the QRS trigger becomes lost while collecting heart images. Once the trigger is relocated, new values should be loaded into the filter's memory buffer.

Another condition that may require resetting is if a mismatch of image frames occurs, as a result of either an extra frame or a shortage of frames in the current cycle. This may be caused by a sudden change in the heart rate or by the QRS trigger occurring close to the start of a new frame. Alternatively, to avoid resetting, the system may be programmed to initially ignore the extra or missing frame, passing through the frames in the memory buffer unfiltered by temporarily setting the constant "c" to be 1, thereby making y(n) equal to y(n−1). Another alternative is to match up the times of new frames as best as possible with the frames in the memory buffer, ignoring the extra or missing frame. However, if the mismatch persists into the next cycle, then it is likely that the mismatch was not a random occurrence, and the filter should be reset.

One preferred technique for deciding when to reset the filter is to perform a frame correlation procedure using the current image frame and the image frame in the memory buffer. If the current image frame is below a predetermined threshold, then the filter would be reset for the particular frame period, or perhaps for all frame periods. This technique is based on the principle that frames acquired at the same point in each cycle should not vary significantly from cycle to cycle, and thus should be highly correlated (i.e., high correlation coefficient). If the current frame is very different from the history of past image frames, then it is likely that a significant change has occurred in the anatomic structure, such as when the operator moves the probe, and past image data should be deleted.

Although the nth-order IIR filter is the preferred filter for the present invention, other filters may be used, and are within the scope of the invention. Other possible filters include linear filters such as finite impulse response filters, and non-linear filters which take the median, minimum or maximum of a plurality of data values.

The cycle to cycle filtering scheme may be easily implemented using the image loops 100, since the frame header 108 already identifies the frame by number. For example, referring to FIG. 20, the frames of cycle 1 would be packaged into image loop 1, and the four frames would be identified in the frame headers of image loop 1. The frames of cycle 2 would be packaged into image loop 2, and the four frames would be identified in the frame headers of image loop 2. The corresponding frames of successive physiologic cycles which must be matched up for filtering are thus readily identifiable, even if the image loops 100 are stored out of sequence. When packaged into loops, the frames within each loop are given successive frame numbers beginning with 0 or 1. Referring to FIG. 20, the frame numbers for cycles 1–3 have repeating sequence numbers of 1–4, instead of numbers 1–2. It is not necessary to use image loops 100 to implement the cycle to cycle filtering scheme. In implementing filtering across physiologic cycles, the raw image data is preferably stored in an image frame memory 138 for playback at other times, or for transmission to another site for playback at the other site. For simplicity, the frame memory 138 is not shown in the figures related to this feature.

Cycle to Cycle Filtering in Doppler Color Flow Imaging

The cycle to cycle filtering scheme may also be used to process Doppler ultrasound image data. In Doppler velocity-mode ultrasound, shifts in frequency between emitted ultrasonic waves and their echoes are used to measure the velocity of moving objects, based on the principle of the Doppler effect. This technique is typically used to examine cardiovascular blood flow. Another Doppler ultrasound technique is called "color flow imaging" which typically uses a "velocity mode," but may also use a "color power mode." In the velocity mode, the pixel values represent direction and velocity of the anatomic structure, or more typically, blood, at the location represented by the pixel, instead of brightness or intensity as in grayscale ultrasound. Each velocity value or ranges of velocity values (and direction) are color-coded to a different color and shade. The velocity values and their direction are displayed on a screen as a multicolored image. In the "color power mode," the power (i.e., magnitude) of the Doppler signal is used to assign values to the pixels. The power is an indication of the strength of blood flow or fluid flow at a particular location. Each power value or ranges of power values are color-coded to a different color and shade. The power values are displayed on a screen as a multicolored image.

Temporal filtering is typically performed in Doppler color flow imaging in both velocity and power modes as it is done for normal gray-scale structure imaging modes (e.g., B-mode). The effect is to produce a less noisy, more uniform and aesthetically pleasing image. However, in Doppler color velocity imaging, the temporal filtering algorithm is typically modified to persist velocities as they decrease in magnitude while passing through (not filtering) velocities that have a higher magnitude (or a different direction) than the present state of the filter. This is the so-called "fast attack" persistence method.

Figure 23:
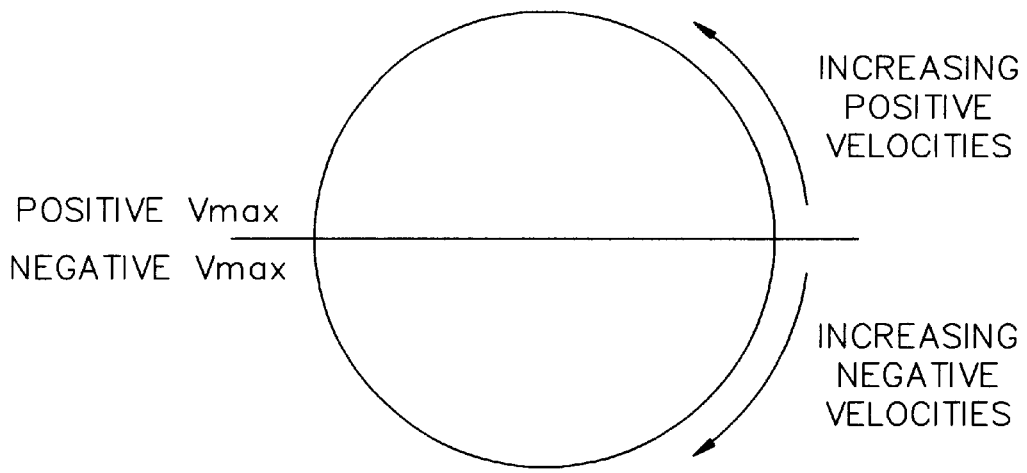
FIG. 23 is a velocity wheel for illustrating how to implement cycle to cycle filtering of Doppler ultrasound image data.

Cycle to cycle filtering may be applied to both of these Doppler imaging modalities as well. In the Doppler power mode, the filtering scheme is exactly the same as described above for B-mode imaging. In Doppler color velocity mode, velocity direction must be considered, primarily to account for "aliasing" of the flow velocity. Aliasing results in an erroneous representation of the true velocity of the blood flow due to sampling at a rate which is less than twice the highest Doppler shift frequency caused by echoes from moving blood. When the mean Doppler shift frequency just exceeds the sampling rate, the velocity will appear to have changed direction. That is, the velocity will wrap around the other side of the velocity wheel (from Positive Vmax to Negative Vmax), as shown in FIG. 23. If the velocity is increased further, it becomes an even smaller magnitude negative velocity value.

In cycle to cycle filtering in the Doppler color velocity mode, the aliasing effect can be addressed in several ways. One way is to use the fast attack persistence method described above. This is not recommended, however, because it is expected that the velocities within each image frame taken from the same point in the physiologic cycle will be very close in value. Therefore, a standard filtering approach is better. (The fast attack persistence method assumes that flow is pulsatile, not constant.) A preferred technique to address the aliasing effect is to "wrap" the data values the shortest distance around the velocity wheel. This is easiest to illustrate in the case of a two-sample average. If both samples represent flow in the same direction, then a simple average is applied. However, if the samples are in the opposite direction, then the resultant average is the value midway between the samples within the segment of the wheel where the distance between the samples is shortest. This method can easily be extended to filter coefficients other than 0.5 (the resultant sample still lies inside the shortest segment of the wheel but is not midway). The preferred embodiment is a first-order IIR filter which this method can also be applied to.

Lastly, the present invention may be used in the prior art area of "image compounding." In image compounding, multiple frames of image data are acquired with different imaging parameters, such as "transmit frequency," and then filtering or otherwise combining this set of images to create a compound image frame. In a conventional scheme, the transmit frequency and/or receiver bandpass filter is varied alternately from frame to frame and then temporal filtering is applied across frames.

Figure 24:
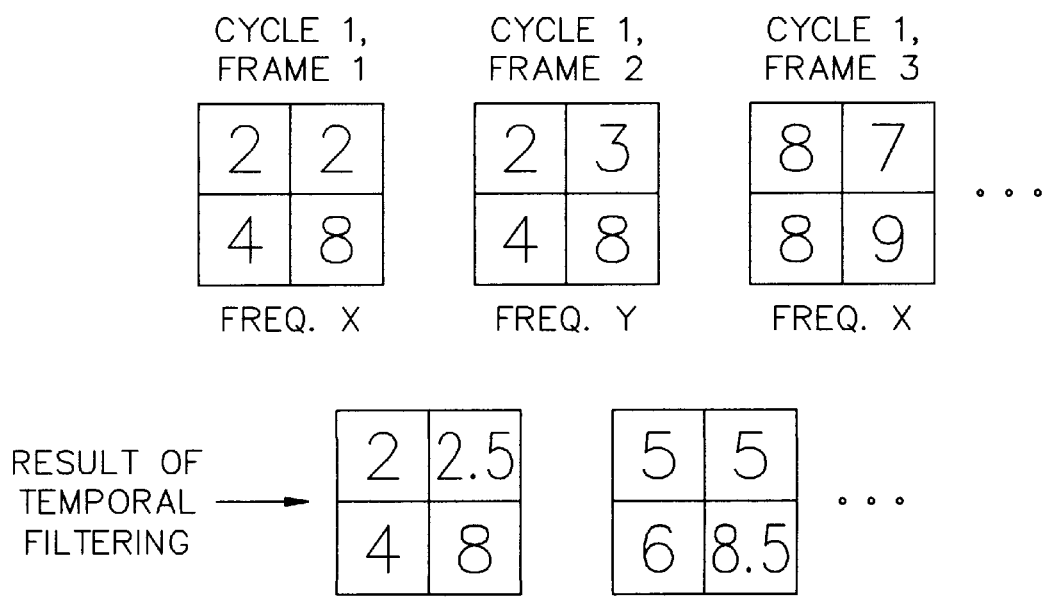
FIG. 24 shows a simplified example of a conventional temporal filtering scheme for implementing frequency-type image compounding.

FIG. 24 shows a simplified example of a conventional temporal filtering scheme for implementing frequency-type image compounding. The filter function in FIG. 24 is a simple averaging filter, wherein $y(n)=\frac{1}{2}x(n)+\frac{1}{2}x(n-1)$. The cycles and frames of FIG. 24 correlate with those of FIG. 20. In FIG. 24, the frequency is toggled between X and Y in successive frames. Since different frequencies cause a variation in the speckle pattern, this technique enhances the speckle reduction performance of the standard temporal filter. However, this scheme also suffers from an inability to accurately represent fast moving anatomic structures. Thus, the frame obtained by temporally filtering frame 2 and frame 3 would not accurately represent the structure, since significant motion has occurred between the acquisition times of the two frames.

Figure 25:
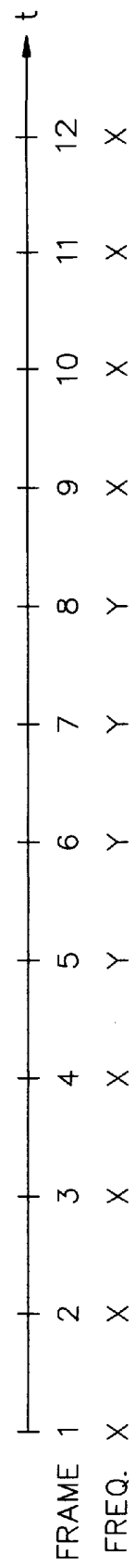
FIG. 25 shows an example of how to implement frequency-type image compounding across a physiologic cycle.

FIG. 25 shows an example of how to implement frequency-type image compounding across a physiologic cycle. The frames in FIG. 25 correspond to the frames in 520. Referring to FIG. 24, the frequency is toggled between X and Y for each physiologic cycle. The pixel processing in FIG. 25 is the same as in FIG. 20. Other types of image compounding are within the scope of the invention, and would be implemented using the same concepts as described with respect to FIG. 25.

Frame Rate Booster

In accordance with another aspect of the present invention, the cycle to cycle filtering scheme may be used to increase the effective frame rate in a medical ultrasound imaging system, and particularly, in a system which acquires imaging data of an anatomic structure having periodic physiological motion, wherein the motion defines successive physiologic cycles.

In echocardiography, some anatomic events are very transient. They may occur only once per heart cycle and are very short-lived, lasting perhaps only 10–30 ms. A high frame rate allows the operator to capture these events. However, there are many limitations on a system's frame rate, such as the speed of sound through tissue, the speed of image processing, display rate, and data storage and transmission requirements. Due to these limitations, image data is often acquired at less than an optimal frame rate, especially in color Doppler mode where several ultrasound pulse transmissions are required to form a single line of data.

Figure 26:
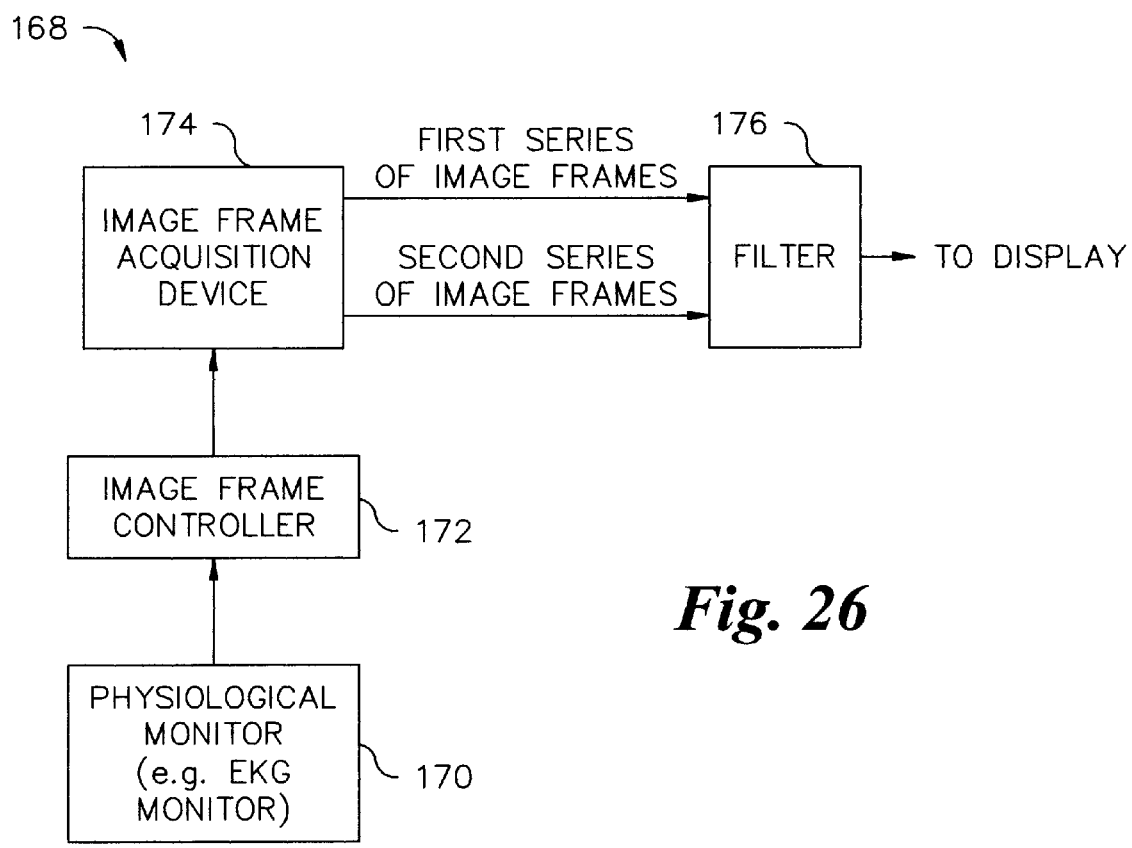
FIG. 26 is a schematic block diagram of a system for increasing the effective acquisition frame rate in a medical ultrasound imaging system in accordance with the present invention.

FIG. 26 shows a system 168 for increasing the effective frame rate. The system 168 includes a physiological monitor 170, an image frame controller 172, an image frame acquisition device 174 (which is generally similar to the acquisition device 134 of FIGS. 6 and 15, except as distinguished below), and a filter 176. The output of the monitor 170 is connected to the input of the image frame controller 172. The output of the image frame controller 172 is connected to a control input of the acquisition device 174. The outputs of the acquisition device 174 are connected to the filter 176. The output of the filter 176 may be connected to an image display (not shown) for viewing the final processed image frames. The outputs of the acquisition device 174 and/or the output of the filter 176 may also be connected to an image frame memory (not shown) for storing either the raw, or processed image data.

The monitor 170 monitors a cyclical physiological parameter associated with the physiologic cycle, and outputs a signal upon the occurrence of a predetermined event in the physiologic cycle. When the imaged structure is the heart, the physiological monitor 170 would be an EKG monitor 160, such as shown in FIG. 15.

The image frame acquisition device 174 acquires imaging data at a fixed frame rate. The device 174 has a processor (not shown, but generally similar to processor 146 of FIGS. 6 and 15) for processing echoes produced from transmission of ultrasound energy into a subject's body. However, unlike the acquisition device 134 of FIGS. 6 and 15, the acquisition device 174 produces at least a first and a second series of image frames for each physiologic cycle. Each image frame comprises data representing an image of a portion of the subject's body taken at a known time with respect to the predetermined event detected by the monitor 170.

Figure 27:
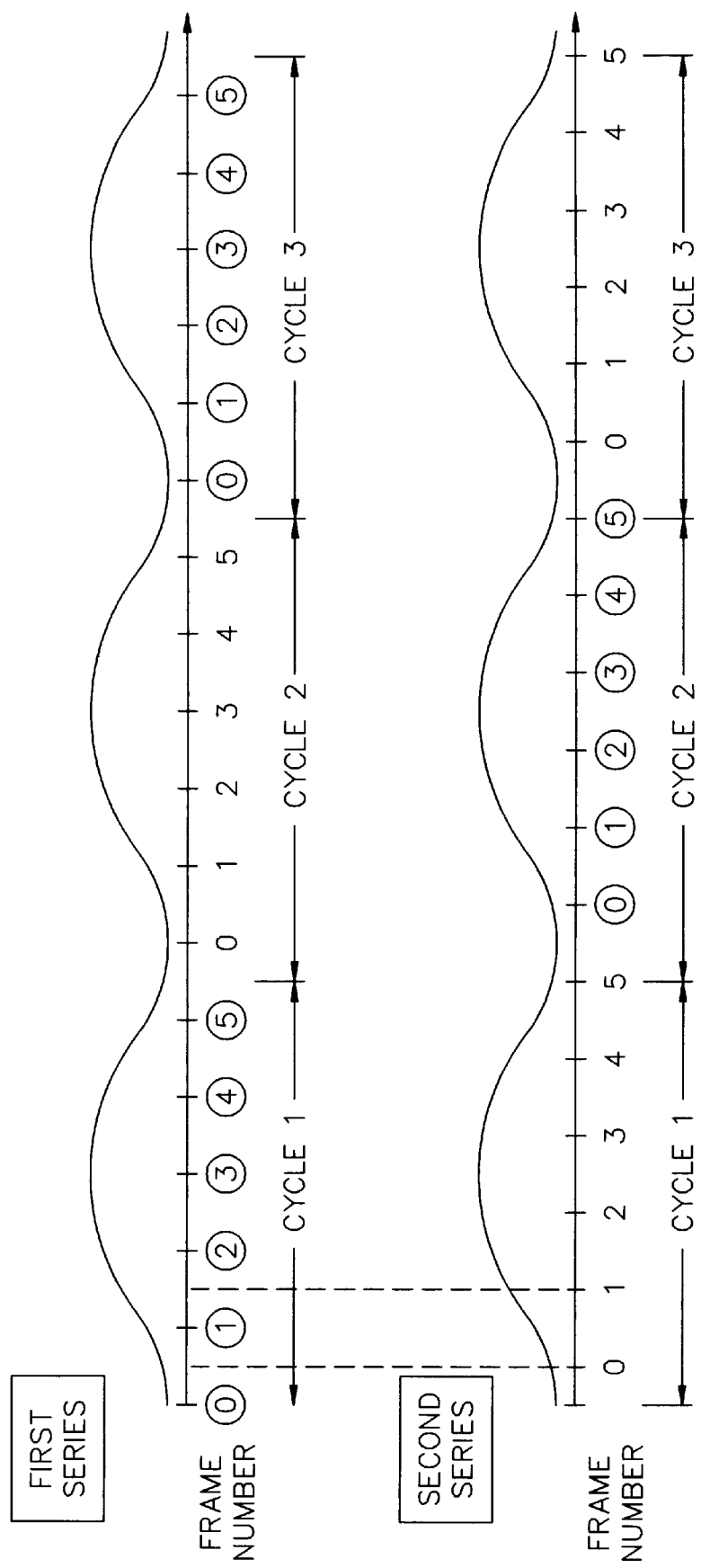
FIG. 27 graphically illustrates the operation of the system of FIG. 26.

FIG. 27 graphically illustrates the function of the image frame controller 172. For illustration purposes, FIG. 27 shows a scheme which acquires five image frames during each periodic physiologic cycle. The frame numbers in this example correspond to the frame number scheme used in image loops. The heart cycle is used in this example, although the illustrated waveform is a generic cyclical pattern. The top graph in FIG. 27 shows a first series of timing intervals for acquiring image frames, and the bottom graph in FIG. 27 shows a second series of timing intervals for acquiring image frames. The frame numbers correspond to the timing intervals. The second series of timing intervals are spaced between the first series of timing intervals. Thus, both the first series and second series have the same frame rate of five frames per cycle.

The image frame controller 172 causes the second series of image frames to be acquired at times between the acquisition of the first series of image frames in an alternating manner. In the example of FIG. 27, the alternating scheme functions as follows:

CYCLE 1: Collect frames 0–5 from first series.
CYCLE 2: Collect frames 0–5 from second series.
CYCLE 3: Collect frames 0–5 from first series.
CYCLE 4 (not shown in FIG. 27): Collect frames 0–5 from second series.

The data collection continues in this manner, alternating between the two series. The circled frames in FIG. 27 show the frames that were acquired.

When obtaining heart images, the timing for frame acquisition may be synchronized to the QRS trigger. For example, acquisition of the first series of image frames may begin exactly at the QRS trigger, and acquisition of the second series of image frames may begin after the QRS trigger, such as at a time halfway between the acquisition time of frames 0 and 1 in the first series of images.

U.S. Pat. No. 5,099,847 (Powers et al.) discloses a frame multiplying scheme which acquires image frames in a manner conceptually similar to FIG. 27. After acquisition, the image frames are displayed as an interleaved sequence of frames, thereby providing an effective display frame rate which is double that of the acquisition device frame rate, in the example given in FIGS. 1 and 2 of this patent. Other multiples of the initial frame rate are possible by collecting additional series of frames, offset from the first and second series by other non-overlapping periods. The scheme of the present invention does not use the image frames to form an interleaved display. Instead, the image frames for successive cycles are subjected to filtering across physiologic cycles, resulting in a new set of image frames which have the same frame rate as the original acquisition device 174, but which incorporate information between the first series of frames that would have been missed without this scheme. Although the scheme in Powers et al. also obtains this extra information, the scheme of the present invention provides an improved, filtered version of the extra information.

To filter across physiologic cycles in the example of FIG. 27 using a simple averaging filter, the following groupings of image frames for the first three cycles are filtered:

Frame 0 of cycle 1, Frame 0 of cycle 2, Frame 0 of cycle 3

Frame 1 of cycle 1, Frame 1 of cycle 2, Frame 1 of cycle 3

Frame 2 of cycle 1, Frame 2 of cycle 2, Frame 2 of cycle 3

Frame 3 of cycle 1, Frame 3 of cycle 2, Frame 3 of cycle 3

Frame 4 of cycle 1, Frame 4 of cycle 2, Frame 4 of cycle 3

In general, the filter 176 thus filters successive image frames obtained at the same point in time within each physiologic cycle. The filter is applied to each image frame within the entire current physiologic cycle, thereby deriving full motion image data. The filter treats the second series of image frames as being located at the same points in time as their respective adjacent first series of image frames. The resultant full motion image data has a higher effective acquisition frame rate than the fixed frame rate of the acquisition device 174. In one preferred filtering scheme, the filter 176 is an nth-order IIR filter function, such as the first order IIR filter 162 shown in FIG. 21.

The concept shown in FIG. 27 may be expanded to collect additional image frame series by using additional physiological event trigger delay times, such as QRS trigger delay times.

The frame rate boosting scheme described herein may also be used in conjunction with the adjustable acquisition frame rate scheme of FIGS. 6–18 to further boost the effective frame rate, while minimizing the collection of redundant information.

Pseudo Real-time Ultrasound Image Transmission Scheme

As discussed above, one advantage of packaging imaging data in image loops 100 is that the image data may be easily transmitted using various communication media, such as the Internet. If the communication medium does not consistently support the full required bandwidth of the real-time data stream of image data, one preferred transmission scheme is to transmit the image loops 100 in pseudo real-time. In this manner, the viewer is presented with temporally accurate image sequences. "Real-time transmission," in the context of the pseudo real-time transmission scheme, thus refers to the ability to display the image data remotely as fast as it is acquired at the patient location site, even though there may be a finite and consistent delay between the viewing time and the acquisition time due to the time required to package and output the image data or due to delays in the transmission medium. Thus, when "real-time transmission" cannot be achieved, there is an inability to view the image display as fast as it is being acquired. Typically, this problem is caused by bandwidth limitations of the transmission medium.

In cardiac imaging, the temporal relationship between image frames is important information in that it is used in the diagnosis of cardiac wall motion abnormalities. The viewer must see image loops that are temporally accurate to represent the true motion of the heart. However, some conventional transmission media do not provide a guaranteed bandwidth (bit rate) for the transmission, and, therefore, do not provide isochronous video. Also, even if the bandwidth is guaranteed, it may fall short of that required by the data stream.

FIG. 28 shows a schematic block diagram of a preferred embodiment of a system 200 for implementing a pseudo real-time transmission scheme. The system 200 is described in the context of heart images acquired in synchronization with an EKG-related trigger, such as a QRS trigger. However, the system 200 may be used for transmitting any type of image data of an anatomic structure having periodic physiological motion, wherein the motion defines successive physiologic cycles and the motion is synchronized to a periodic physiologic event in the cycle. To ensure that the ultimately displayed image data is accurate, the system 200 should have the ability to transmit the image data in at least near real time. When using the system 200, image frames are tagged with actual frame-to-frame timing information, as well as a frame number corresponding to a particular phase of the cardiac cycle. That is, the frame number is resynchronized at each new cardiac cycle. The system 200 includes an image frame acquisition device 202 at a patient location, similar to the acquisition devices disclosed in FIGS. 5 or 6. In one preferred scheme, the image frames are preferably packaged as image loops 100, described above with respect to FIGS. 3A–3C and FIG. 4. Thus, the output of the acquisition device 202 is a series of image loops 100. As discussed above, the image loops 100 may be packaged using image frames acquired from only a single physiological cycle, or from portions of adjacent physiologic cycles.

Referring to FIG. 28, the output of the acquisition device 204 is communicated to a first ping-pong memory 204 at the patient location. The first ping-pong memory 204 has two buffers 206 and 208 for temporarily storing consecutively acquired image loops. The buffers are referred to herein as loop A and loop B, respectively. The first ping-pong memory 204 also includes an input multiplexer or input switch 210 connected at its input to the output of the acquisition device 204, and connected at a first and second output to respective inputs of the buffers 206 and 208. The first ping-pong memory 204 also includes an output demultiplexer or output switch 211 connected at its input to the respective outputs of the buffers 206 and 208, and connected at its output to a transmission medium 212. The transmission medium 212 connects the patient location to a remote location. At the remote location, the system 200 includes a second ping-pong memory 214, similar to the first ping-pong memory 204. Thus, the second ping-pong memory 214 has two buffers 216 and 218 for temporarily storing consecutively acquired image loops. The buffers are referred to herein as loop C and loop D, respectively. The second ping-pong memory 214 also includes an input multiplexer or input switch 220 connected at its input to the transmission medium 212, and connected at a first and second output to respective inputs of the buffers 216 and 218. The second ping-pong memory 214 also includes an output demultiplexer or output switch 222 connected at its input to the respective outputs of the buffers 216 and 218, and connected at its output to a remote viewing station or remote image display 224 for providing the real-time or pseudo real-time image of the subject's body. The ping-ping memories 204 and 214 are conventional, and thus are not described in further detail.

At the patient location, the scheme functions as follows:
(1) Upon initiation of image data acquisition, the switch 210 is connected to the loop A buffer for filling the loop A buffer with image data.
(2) When the loop A buffer becomes filled with a full physiologic cycle of image data (e.g., one image loop), the switch 210 is switched to the loop B buffer and the switch 211 is switched to the loop A buffer.
(3) Upon switching, the image loop in the loop A buffer is transmitted, and the loop B buffer fills with new image data. The loop B buffer is written over and over again until the transmission of image data from the loop A buffer is completed.
(4) When the transmission of image data from the loop A buffer is completed and the loop B buffer contains a loop of new data, the switch 210 is switched to the loop A buffer to fill the loop A buffer with new image data, and the switch 211 is switched to the loop B buffer to transmit the image loop in the loop B buffer. Steps (3) and (4) are continuously repeated until data transmission is stopped.

At the remote location, the scheme functions as follows:
(1) The switch 220 is switched to the loop C buffer, and the loop C buffer receives the image loop transmitted from the loop A buffer in step (3) above.
(2) When the transmission is completed, the switch 220 switches to the loop D buffer to allow the loop D buffer to receive the next transmission of image data, and the switch 222 is switched to the loop C buffer, thereby allowing the contents of the loop C buffer to be displayed on the image display 224. The image loop in the loop C buffer is continuously played (i.e., looped) until the loop D buffer is filled with a new image loop.
(3) When the loop D buffer becomes filled with a new image loop, the switch 220 switches to the loop C buffer to allow the loop C buffer to receive the next transmission of image data, and the switch 222 is switched to the loop D buffer, thereby allowing the contents of the loop D buffer to be displayed on the image display 224. Again, the image loop in the loop D buffer is continuously played (i.e., looped) until the loop C buffer is filled with a new image loop. Steps (2) and (3) are continuously repeated until data transmission is stopped.

The loop A and loop B buffers alternately function as "capture buffers" and "transmit buffers," whereas the loop C and loop D buffers alternately function as "receive buffers" and "display buffers."

If the transmission medium bandwidth fully supports the image data rate, then the display will be a true real-time representation of the image data and no "looping" or image data overwriting would occur. If the bandwidth is inadequate, even for brief periods, the viewed image display will not be interrupted. Since the physiologic cycles are assumed to be periodic and very similar from cycle to cycle, the repetition of a cycle from time to time or periodically (e.g., two to four loops for each cycle on a consistent basis) still provides an accurate representation of the temporal nature of the image.

The sender's outgoing data buffer (first ping-pong memory 204) should be large enough to store up to two cycles of image data so that while one cycle is being transmitted, new image data may be written into the buffer simultaneously. However, if it takes longer than one cycle to empty the transmit buffer, the new data from the next cycle will be overwritten with the following cycle of data so that the data in the capture buffer does not continue to grow. This, in effect, adapts the amount of transmitted data to the actual bandwidth being provided by the transmission medium without having to know the actual bandwidth beforehand. Also, this ensures that the receiving station (remote location) is always updated with the most recent image data.

To minimize the idle time of the transmission medium 212 and to allow the displayed image data to be as current as possible, it is preferred to use a cyclical memory for the loop A–D buffers. A cyclical memory allows image loops to be packaged by physiologic cycles, but not necessarily using image data from the same cycle. This idea is discussed above in the example of four physiologic cycles, A–D, wherein four image frames 1–4 are taken per cycle, and the image loops include portions of adjacent cycles (e.g., Image loop 1—B1 B2 A3 A4; Image loop 2—C1 C2 B3 B4; Image loop 3—D1 D2 C3 C4). In this manner, when the data transmission is completed, the new transmit buffer can immediately send its image loop, even if the current physiologic cycle has not been completed.

FIG. 29 shows a schematic block diagram of an alternative system 184 for implementing a pseudo real-time transmission scheme. Referring to FIG. 29, the output of the acquisition device 204 is communicated to a first buffer or memory 186 at the patient location. The first memory 186 has two buffers 188 and 190. The buffers are referred to herein as loop A and loop B, respectively. The loop A buffer receives the output of the acquisition device 204, and thus is connected to the input of the first memory 186. The loop A buffer thus acts as the "capture buffer." The output of the first memory 186 is the output of the loop B buffer and is communicated via communication or transmission medium 192 to an input of a second buffer or memory 194. The loop B buffer thus acts as the "transmit buffer." The second memory 194 also has two buffers 196 and 198. The buffers are referred to herein as loop C and loop D, respectively. The loop C buffer receives the output of the loop B buffer, and thus acts as the "receive buffer." The output of the second memory 194 is the output of the loop D buffer, and is communicated to a remote viewing station or remote image display 200 for providing the real-time or pseudo real-time image of subject's body. The loop D buffer thus acts as the "display buffer."

At the patient location, the scheme functions as follows:
(1) The image data in the loop B buffer is transmitted to the loop C buffer.
(2) The loop A buffer is written over and over again until the transmission of image data from the loop B buffer is completed.
(3) When the transmission of image data from the loop B buffer is completed, the most recent full loop of image data in buffer A is transferred to the loop B buffer for immediate transmission, and the loop A buffer begins to fill again.

At the remote location, the scheme functions as follows:
(1) The loop C buffer receives the loop B image data and transfers it to the loop D buffer after a full image loop is received in the loop C buffer.
(2) The image data in loop D is continuously played (i.e., looped) until the loop C buffer receives another full image loop.
(3) Next, the latest full loop of image data in loop C is immediately transferred to loop D for continuous playing until loop C receives and transfers the next full image loop.

FIGS. 30A and 30B show sample contents of the loop A–D buffers in FIGS. 28 and 29 for the first fourteen successive physiologic cycles obtained by the acquisition device 204 in a session. In the example of FIG. 30A, the bandwidth of the transmission medium 192 is sufficient to support real-time image display. Therefore, the image data in the loop D buffer, which is output to the image display 200, is identical in sequence to the image data in the loop A buffer. Even though there is a delay of three physiologic cycles between acquisition of the image data at the patient location and display of the image data at the remote location, all of the image data is displayed exactly as it was collected. In the example of FIG. 30B, the bandwidth of the transmission medium 192 is insufficient to support real-time image display. In this example, exactly one physiologic cycle of image data may be transmitted from the loop B buffer to the loop C buffer in the time that it takes to collect exactly three physiologic cycles of image data. Thus, the loop D buffer loops three times through each physiologic cycle of image data, skipping two cycles of image data between each displayed cycle of image data. Note, also, that the loop B buffer transmits only the latest available image data. During the transmission time, any image data which cannot be transferred from the loop A buffer to the loop B buffer is discarded.

Means for performing the data transferring and transmitting functions of the memories 204 and 214 in the first embodiment, and the memories 186 and 194 in the second embodiment, should be well understood by an artisan familiar with such memories, in view of the description provided herein of its functions.

The preferred embodiment of the pseudo real-time transmission scheme uses image loops 100 having the structure shown in FIGS. 3A–3C and FIG. 4. However, the image data may be collected, organized or packaged in conventional ways, as long as the beginning and end points, or a triggering event, of the physiologic cycles are identifiable, and the scope of the pseudo real-time transmission scheme includes the transmission of image data collected, organized or packaged in conventional ways.

The preferred embodiment of the pseudo real-time transmission scheme uses two ping-pong memories. However, other types of memory structures which provide the highlighted functions of the ping-pong memories may be used and are within the scope of the invention.

The pseudo real-time transmission scheme is equally effective in transmitting and remotely viewing other types of non-image-related periodic physiological data, such as EKG waves.

The inventions set forth above may also be applied to medical imaging systems other than ultrasound which acquire full motion image data of moving anatomic structures. For example, nuclear magnetic resonance (NMR) or magnetic resonance imaging (MRI), computerized axial tomography (CAT), positron emission tomography (PET), and the like acquire discrete scan lines of imaging data for reconstruction into a full-frame image of the body parts. These scan lines may be packaged into image loops. Likewise, the frame rates of the image frames may be adjusted using any of the techniques described above to reduce the amount of acquired data, without compromising image quality. Furthermore, the image frames acquired by such systems may be filtered across physiologic cycles, instead of temporally, to reduce image artefacts.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An image frame memory for storing ultrasound image frame data obtained from an anatomic structure having periodic physiological motion, the motion defining successive physiologic cycles, the memory storing the image frame data as a plurality of image loops, each image loop including frame data representing a plurality of image frames acquired at spaced time intervals within a physiologic cycle.

2. An image frame memory for storing ultrasound image frame data obtained from an anatomic structure having periodic physiological motion, the motion defining successive physiologic cycles, the memory storing the image frame data as a plurality of image loops, each image loop comprising:

(a) a loop header including a loop identification number; and (b) a plurality of frame packets, each frame packet including a frame header including a frame number within the image loop, and frame data representing one image frame acquired at a spaced interval within the physiologic cycle.

3. A method of communicating ultrasound imaging data acquired by medical ultrasound imaging equipment from a first location to a second location, the imaging data being acquired from an anatomic structure having periodic physiological motion, the motion defining successive physiologic cycles, the method comprising:

(a) formatting the imaging data as a plurality of image loops, each image loop including image frame data representing a plurality of image frames acquired at spaced time intervals within a physiologic cycle; and (b) communicating the image loops from the first location to the second location via a transmission medium.

4. The method of claim 3 wherein the first location includes a memory having (i) a first buffer, and (ii) a second buffer, the first and second buffers of the first location alternately functioning as a capture buffer and a transmit buffer in an opposite manner with respect to each other, and the second location includes a memory having (i) a third buffer, and (ii) a fourth buffer, the third and fourth buffers of the second location alternately functioning as a receive buffer and a display buffer in an opposite manner with respect to each other, wherein steps (a) and (b) further comprise:

(i) storing the image loop data in the first buffer as it is being acquired, the first buffer repeatedly overwriting its stored image loop data with new image loop data for each successive physiologic cycle, (iii) communicating the image loop in the first buffer to the third buffer via the transmission medium when a new image loop is collected in the first buffer and when the second buffer completes the communication of its currently stored image loop, the first and second buffers thereby switching functions upon completion of the communication by the first buffer, (iv) outputting the image loop in the third buffer to an image display at the second location when the third buffer receives the entire image loop from the first buffer, the image loop currently in the fourth buffer being repeatedly displayed until it is overwritten with the next complete image loop received from the first or the second buffer, the third and the fourth buffers thereby switching functions upon receipt of a new image loop from the first or second memory, the imaging data thereby being displayed in real-time whenever the bandwidth of the transmission medium is sufficient to allow step (iv) to always be completed in a time period which does not exceed one physiologic cycle, the imaging data being displayed in pseudo real-time whenever the bandwidth of the transmission medium is insufficient to allow step (iv) to be completed in a time period which does not exceed one physiologic cycle.

5. The method of claim 3 wherein the first location includes a memory having (i) a capture buffer, and (ii) a transmit buffer, and the second location includes a memory having (i) a receive buffer, and (ii) a display buffer, wherein steps (a) and (b) further comprise:

(i) storing the imaging data in the capture buffer as it is being acquired, the capture buffer repeatedly overwriting its stored imaging data with new imaging data for each successive physiologic cycle, (ii) transferring the imaging data in the capture buffer to the transmit buffer when a complete image loop of imaging data is collected in the capture buffer and when the transmit buffer becomes ready to receive a new image loop, (iii) communicating the image loop in the transmit buffer to the receive buffer via the transmission medium, the transmit buffer becoming ready to receive its new image loop from the capture buffer upon completion of the communication, (iv) transferring the image loop in the receive buffer to the display buffer when a complete image loop of imaging data is collected in the receive buffer; and (v) outputting the image loop in the display buffer to an image display at the second location for viewing the acquired imaging data, the image loop currently in the display buffer being repeatedly displayed until it is overwritten with the next complete image loop transferred from the receive buffer, the imaging data thereby being displayed in real-time whenever the bandwidth of the transmission medium is sufficient to allow step (iv) to always be completed in a time period which does not exceed one physiologic cycle, the imaging data being displayed in pseudo real-time whenever the bandwidth of the transmission medium is insufficient to allow step (iv) to be completed in a time period which does not exceed one physiologic cycle.

6. A method of increasing the effective acquisition frame rate in a medical ultrasound imaging system which acquires imaging data of an anatomic structure having periodic physiological motion, the motion defining successive physiologic cycles, the method comprising:

(a) monitoring a cyclical physiological parameter associated with the physiologic cycle, and obtaining a signal upon the occurrence of a predetermined event in the physiologic cycle;

(b) using an image frame acquisition device to acquire imaging data at a fixed acquisition frame rate, the acquisition device processing echoes produced from transmission of ultrasound energy into a subject's body, the acquisition device producing at least a first and a second series of image frames for each physiologic cycle, each image frame comprising data representing an image of a portion of the subject's body taken at a known time with respect to the predetermined event;

(c) acquiring the second series of image frames at times between the acquisition of the first series of image frames in an alternating manner by using the signal obtained upon the occurrence of a predetermined event in the physiologic cycle to time the image data acquisition; and (d) filtering successive image frames obtained at the same point in time within each physiologic cycle using a filter, the filter being applied to each image frame within the current physiologic cycle, thereby deriving full motion image data, wherein the filter treats the second series of image frames as being located at the same points in time as their respective adjacent first series of image frames, the resultant full motion image data having a higher effective acquisition frame rate than the fixed acquisition frame rate of the acquisition device.

7. A method according to claim 6 wherein the physiologic cycle is the heart cycle, and the predetermined event in the physiologic cycle is the QRS trigger, the first and second series of image frames thereby being taken at different known times with respect to the QRS trigger.

8. An apparatus for increasing the effective acquisition frame rate in a medical ultrasound imaging system which acquires imaging data of an anatomic structure having periodic physiological motion, the motion defining successive physiologic cycles, the apparatus comprising:

(a) a physiological monitor for monitoring a cyclical physiological parameter associated with the physiologic cycle, and for outputting a signal upon the occurrence of a predetermined event in the physiologic cycle;

(b) an image frame acquisition device which acquires imaging data at a fixed acquisition frame rate, the acquisition device having a processor for processing echoes produced from transmission of ultrasound energy into a subject's body, the acquisition device producing at least a first and a second series of image frames for each physiologic cycle, each image frame comprising data representing an image of a portion of the subject's body taken at a known time with respect to the predetermined event;

(c) a controller for the image frame acquisition device connected to the physiological monitor for causing the second series of image frames to be acquired at times between the acquisition of the first series of image frames in an alternating manner; and (d) a filter for filtering successive image frames obtained at the same point in time within each physiologic cycle, the filter being applied to each image frame within the current physiologic cycle, thereby deriving full motion image data, wherein the filter treats the second series of image frames as being located at the same points in time as their respective adjacent first series of image frames, the resultant full motion image data having a higher effective acquisition frame rate than the fixed acquisition frame rate of the acquisition device.

9. An apparatus according to claim 8 wherein the physiologic cycle is the heart cycle, and the predetermined event in the physiologic cycle is the QRS trigger, the first and second series of image frames thereby being taken at different known times with respect to the QRS trigger.

* * * * *